(12) United States Patent
Lee et al.

(10) Patent No.: US 7,521,221 B2
(45) Date of Patent: Apr. 21, 2009

(54) STAPHYLOCOCCUS AUREUS STRAIN CYL1892

(75) Inventors: Chia Y. Lee, Little Rock, AR (US); Thanh T. Luong, Little Rock, AR (US)

(73) Assignee: Board of Trustees of the University of Arknasas, Little Rock, AR (US)

( * ) Notice: Subject to any disclaimer, the term of this patent is extended or adjusted under 35 U.S.C. 154(b) by 0 days.

(21) Appl. No.: 11/285,700

(22) Filed: Nov. 21, 2005

(65) Prior Publication Data

US 2007/0166803 A1 Jul. 19, 2007

(51) Int. Cl.
- *G01N 33/569* (2006.01)
- *C12P 21/04* (2006.01)
- *C12P 19/04* (2006.01)
- *C12P 21/06* (2006.01)
- *C07H 5/04* (2006.01)

(52) U.S. Cl. .................. 435/252.3; 435/72; 435/101; 435/69.1; 435/7.33; 536/55.1; 536/23.7

(58) Field of Classification Search .................. None
See application file for complete search history.

(56) References Cited

U.S. PATENT DOCUMENTS

2005/0013872 A1 1/2005 Freyman

FOREIGN PATENT DOCUMENTS

WO  WO 2005009498  2/2005

OTHER PUBLICATIONS

Luong et al. Overproduction of type 8 capsular polysaccharide augments *Staphylococcus aureus* virulence. Infn. Immun., 2002, vol. 70 (7): 3389-3395.*
Sau et al., The *Staphylococcus aureus* allelic genetic loci for serotype 5 and 8 capsule expression contain the type -specific genes flanked by common genes. Microbiology, 1997, vol. 143: 2395-2405.*
Luong, T. and Lee, C., Overproduction of Type 8 Capsular Polysaccharide Augments *Staphylococcus aureus* Virulence,Infection and Immunity, Jul. 2002, p. 3389-3395 vol. 70, No. 7.
S. Sau, J. Sun and C.Y. Lee., Molecular charactarization and transcriptional analysis of type 8 capsule genes in *Staphylococcus aureus*, J. Bacteriol. 179:1614-1621. (1997).
Tamama et al, Epidermal growth factor as candidate for ex vivo expansion of bone marrow-derived mesenchymal stem cells, Stem Cells Express, Sep. 8, 2005, pp. 1-40.
ISR for PCT/US08/51598 dated Aug. 15, 2008.

* cited by examiner

*Primary Examiner*—Rebecca E. Prouty
*Assistant Examiner*—Ganapathirama Raghu

(57) ABSTRACT

This disclosure presents embodiments of novel strains of *Staphylococcus aureus* that through genetic engineering produce type 5 capsular polysaccharide at greater levels than *Staphylococcus aureus* strain Reynolds.

7 Claims, 6 Drawing Sheets

PCR Primer Sequences

| | | |
|---|---|---|
| Ppa5ar1 | 5'-GGATCCCCTTTTACCTGCACCAGGCTTTTC-3' | (SEQ ID NO:8) |
| Ppa5r2 | 5'-CCATGGCTCTAAAGTAGTAATAGTTTG-3' | (SEQ ID NO:9) |
| Ppa1r | 5'-TTCTAATGTACTTTCCATATAAACCTCCTATTTTCC-3' | (SEQ ID NO:10) |
| Ppa8af7 | 5'-AAATAGGAGGTTTATATGGAAAGTACATTAGAATTA-3' | (SEQ ID NO:11) |
| Ppa8f8 | 5'-GAATTCGAGTCTACAAGCGATTAAA-3' | (SEQ ID NO:12) |
| Ppa1fNcoI | 5'-CGGCCATGGCCACAGTATAAATTATATCAG-3' | (SEQ ID NO:13) |

*Fig. 1*

STAPHYLOCOCCUS AUREUS STRAIN CYL1892

REFERENCE TO "SEQUENCE LISTING" SUBMITTED ON CD

This specification is accompanied by an original compact disc and one identical copy, the contents of which are hereby incorporated by reference. The compact discs each contain the file: 5339-9952.txt.

BRIEF DESCRIPTION OF THE DRAWINGS

FIG. 1 illustrates the DNA sequences of primers utilized in various Polymerase Chain Reaction ("PCR") procedures for construction of a modified 5' control region for the cap5 operon of *Staphylococcus aureus* in which the cap1 promoter replaces the cap5 promoter. The DNA sequences are identified as SEQ ID NO:8, SEQ ID NO:9, SEQ ID NO:10, SEQ ID NO:11, SEQ ID NO:12, and SEQ ID NO:13.

FIG. 2A illustrates the location of PCR primers relative to the modified 5' control region DNA sequence. FIG. 2B illustrates the nature of the various DNA sequences of the modified 5' control region.

FIG. 4 illustrates the modified 5' control region integrated into the *Staphylococcus aureus* strain Reynolds genome to create a new strain of *Staphylococcus aureus* comprising a cap5 operon operably linked to a cap1 promoter.

FIG. 6 also illustrates the difference in type 5 capsular polysaccharide production between strain Reynolds and strain CYL 1982 when grown on solid media.

DESCRIPTION

Figure 2:
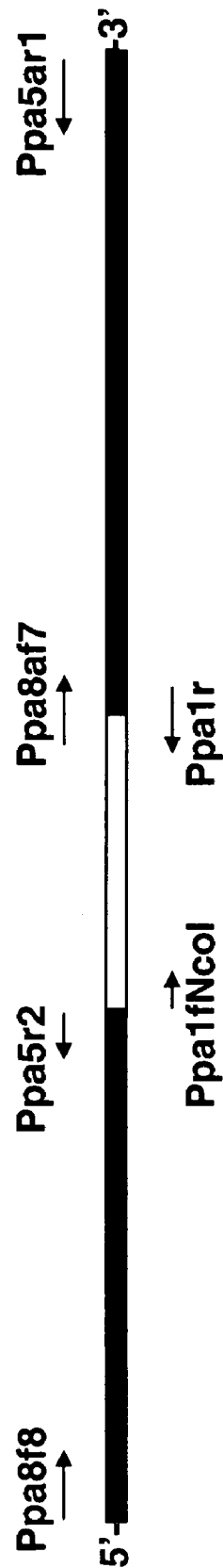
FIG. 2 illustrates the PCR-based cloning strategy utilized for replacing the cap5 promoter with the cap1 promoter. Specifically.
Figure 2:
Figure 3:
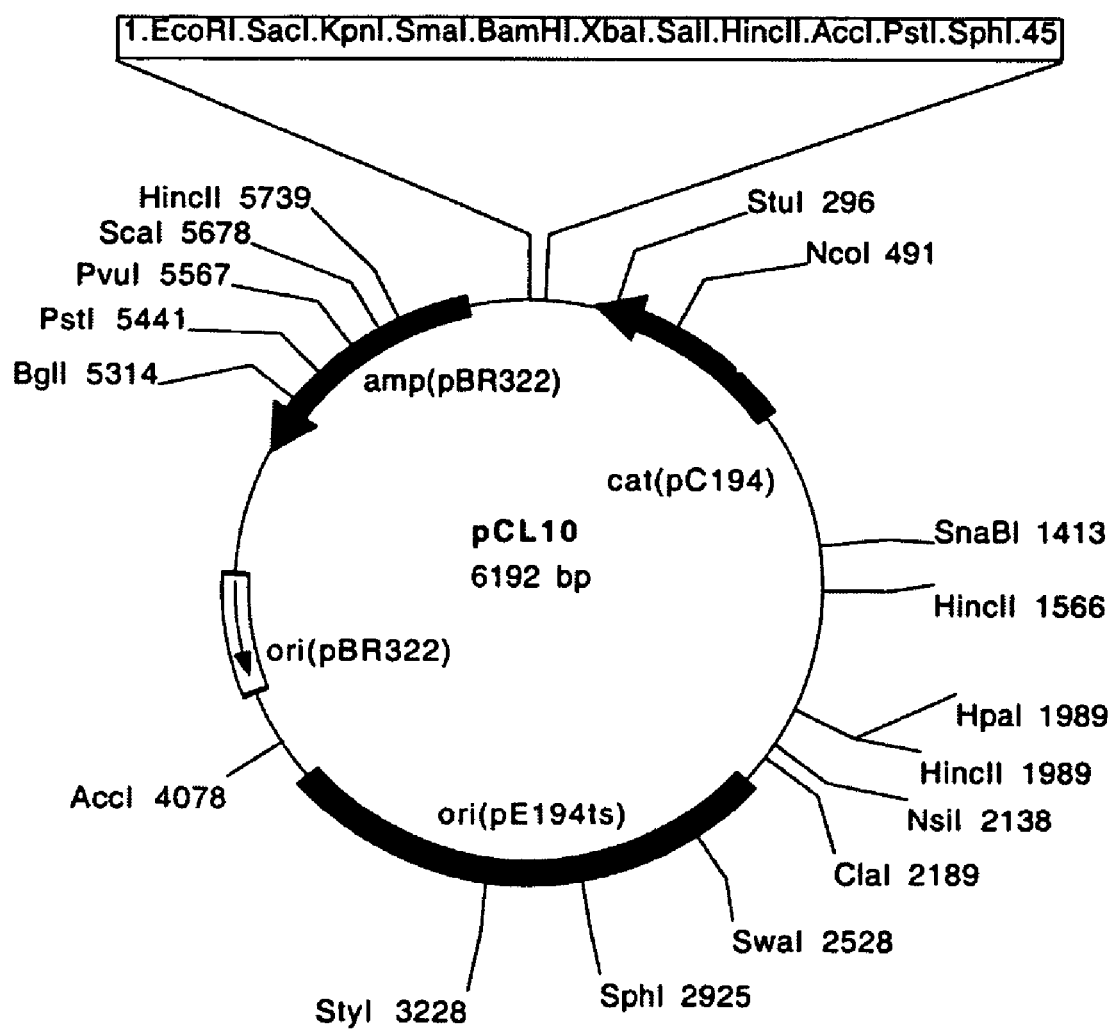
FIG. 3 illustrates a map of the shuttle vector pCL10 utilized in construction of the modified 5' control region for the cap5 operon.
Figure 4:
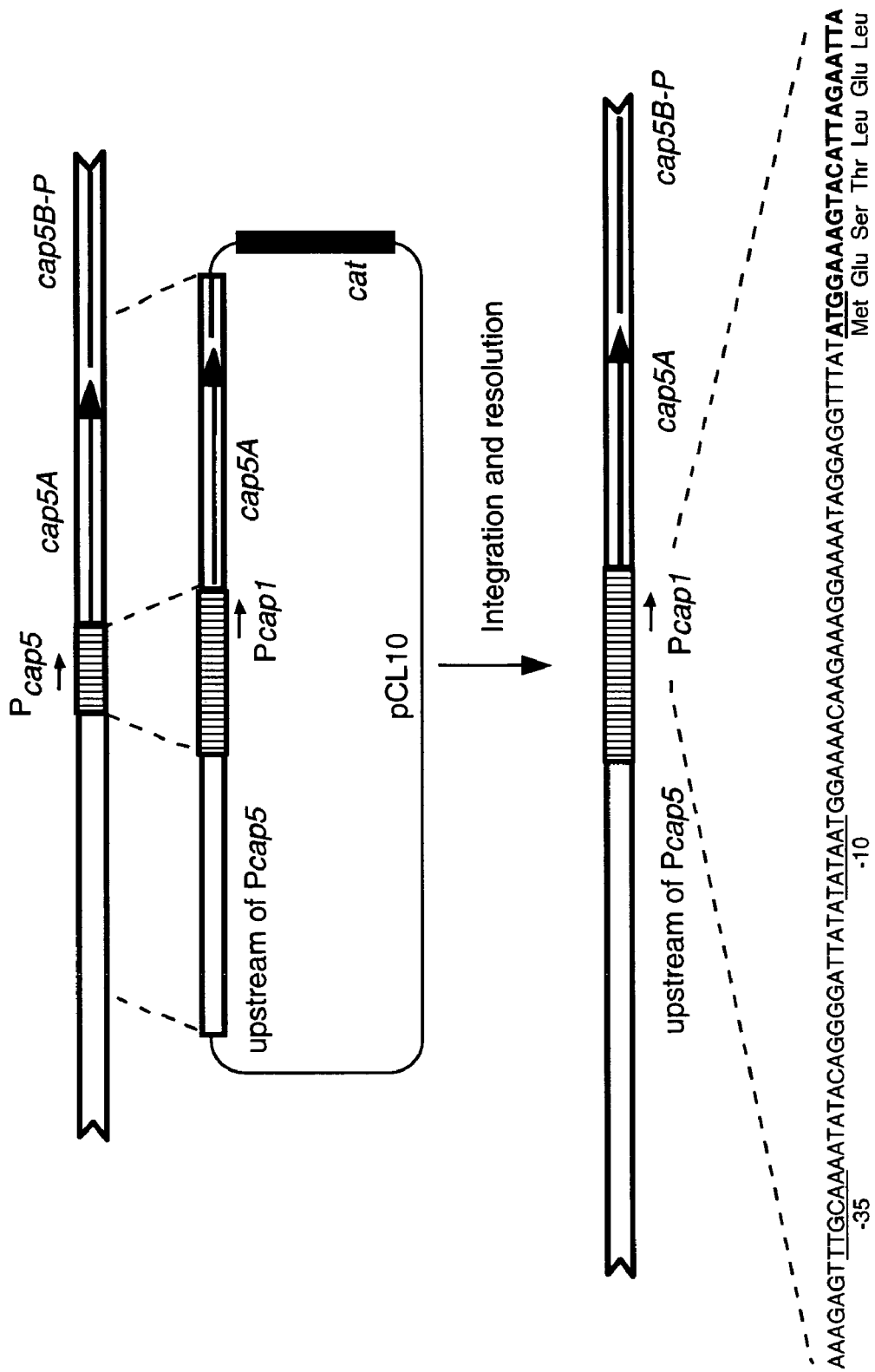
FIG. 4 illustrates the modified 5' control region ligated into the shuttle vector pCL10 in relation to the native cap5 operon of *Staphylococcus aureus* strain Reynolds. Additionally.

This disclosure presents embodiments of novel strains of *Staphylococcus aureus* ("*S. aureus*") and uses thereof.

In various embodiments of the present invention, the cap5 operon of *S. aureus* is controlled by a constitutive promoter. In various embodiments of the present invention, said constitutive promoter is the cap1 promoter from *S. aureus* strain M. In various embodiments of the present invention, the strains of *S. aureus* encompassed by this disclosure produce type 5 capsular polysaccharide at greater levels than wild-type *S. aureus* strain Reynolds.

One embodiment of the present invention comprises CYL1892, a novel strain of *S. aureus*.

In one embodiment of the present invention, the cap5 operon comprises the genes cap5A through cap5P. In one embodiment of the present invention, the cap5 operon comprises the genes cap5A through cap5O. In various embodiments of the present invention, the cap5 operon comprises genes encoding proteins involved in the synthesis of type 5 capsular polysaccharide.

In various embodiments of the present invention, a method of producing type 5 capsular polysaccharide is disclosed wherein said method comprises culturing a strain of *S. aureus* encompassed by various embodiments of the present invention and obtaining type 5 capsular polysaccharide from the culture.

One embodiment of the present invention provides a deoxyribonucleic acid ("DNA") sequence comprising a 5' flanking region of the cap5 promoter linked to a cap1 promoter operably linked to a 3' flanking region of the cap5 promoter wherein said DNA sequence comprises a modified 5' control region. A promoter is operably linked to a DNA sequence if the promoter is joined to said DNA sequence in a manner capable of promoting transcription of the DNA sequence.

One embodiment of the present invention provides a DNA sequence comprising a modified 5' control region operably linked to a cap5 operon. Yet another embodiment provides a strain of *S. aureus* comprising a modified 5' control region operably linked to a cap5 operon wherein said strain of *S. aureus* produces approximately 11.5 fold more type 5 capsular polysaccharide than *S. aureus* strain Reynolds.

In various embodiments of the present invention, type 5 capsular polysaccharide comprises the structure→4)-β-D-ManNAcA(1→4)-α-L-FucNAc(3OAc)-(1→3)-β-D-FucNAc(1→.

In one embodiment of the present invention, the DNA primers listed in FIG. 1 may be utilized in Polymerase Chain Reactions to produce DNA sequences for construction of a constitutive promoter operably linked to a cap5 operon.

The forward primer Ppa8f8 (SEQ ID NO:12) and reverse primer Ppa5r2 (SEQ ID NO:9) are partially complementary to the genomic DNA of *S. aureus* strain Reynolds. PCR reactions using these primers and *S. aureus* strain Reynolds genomic DNA as template produce a 778 base pair ("bp") PCR product, SEQ ID NO:1. The PCR product identified as SEQ ID NO:1 comprises a DNA sequence that is substantially similar to a portion of the 5' flanking region of the cap5 operon of *S. aureus* strain Reynolds. The 5' flanking region of the cap5 operon is any sequence of DNA that is no more than about 10,000 bases, no more than about 5,000 bases, no more than about 4,000 bases, no more than about 3,000 bases, no more than about 2,000 bases, or no more than about 1,000 bases 5' to the cap5 promoter of the cap5 operon or DNA that is substantially similar to the 5' flanking region of the cap5 operon. Substantially similar DNA sequences are DNA sequences that have at least about 80% identity. While it is recognized that SEQ ID NO:1 was used in the construction of the modified 5' control region of one embodiment of the present invention, it is envisioned that other sequences of the 5' flanking region of the cap5 operon could be utilized to achieve substantially the same results in other embodiments. Therefore, the use of SEQ ID NO:1 should not be construed as limiting.

In various embodiments of the present invention, the cap5 promoter of the cap5 operon is replaced by a constitutive promoter. A constitutive promoter encompassed by embodiments of the present invention includes the cap1 promoter. It is envisioned that other constitutive promoters may be used in various embodiments of the present invention including, but not limited to, promoters that are substantially similar to the cap1 promoter. It is also envisioned that other sequences comprising the cap1 promoter may be used in various embodiments of the present invention. Therefore, the examples recited should not be construed as limiting the scope of the disclosure.

The promoter of the cap1 operon of *S. aureus* strain M is known to be a constitutive promoter. In one embodiment of the present invention, the cap5 promoter of *S. aureus* strain Reynolds has been replaced with the cap1 promoter of *S. aureus* strain M. The forward primer Ppa1fNcoI (SEQ ID NO:13) and reverse primer Ppa1r (SEQ ID NO:10) are partially complementary to the genomic DNA of *S. aureus* strain M. PCR using these primers and *S. aureus* strain M genomic DNA as template produces a 250 bp PCR product, SEQ ID NO:2. In various embodiments of the present invention, the cap1 promoter of *S. aureus* strain M comprises the DNA sequence identified by SEQ ID NO:2.

In one embodiment of the present invention, a 3' flanking region of the cap5 promoter has been amplified by PCR. A 3' flanking region of the cap5 promoter may be a DNA sequence of the cap5 operon that is located 3' to the cap5 promoter including, but not limited to, any sequence comprising about the first 50 bases 3' to the cap5 promoter, about the first 100 bases 3' to the cap5 promoter, about the first 500 bases 3' to the cap5 promoter, about the first 1,000 bases 3' to the cap5 promoter, about the first 2,000 bases 3' to the cap5 promoter, about the first 5,000 bases 3' to the cap5 promoter, or about the first 10,000 bases 3' to the cap5 promoter or portions thereof.

PCR using the primers Ppa8af7 (SEQ ID NO:11) and Ppa5ar1 (SEQ ID NO:8) and *S. aureus* strain Reynolds genomic DNA as template produces an 872 bp PCR product that spans the cap5A gene and a partial cap5B gene. The 3' flanking region of the cap5 promoter comprises the 872 bp PCR product and is identified as SEQ ID NO:3. Although the 872 bp 3' flanking region of the cap5 promoter has been used in some embodiments of the present invention, it is envisioned that other sequences that are 3' to the cap5 promoter may be used to create a 3' flanking region. Additionally, it is envisioned that DNA sequences that are substantially similar to the 3' flanking region of the cap5 promoter may be used in various embodiments of the present invention. Therefore, the example should not be construed as limiting.

The DNA comprising SEQ ID NO:2 (250 bp cap1 promoter) has been joined to the DNA comprising SEQ ID NO:3 (872 bp 3' flanking region of the cap5 promoter) by overlapping PCR according to the method of Higuchi. (1) The PCR primer Ppa8af7 (SEQ ID NO:11) is partially complementary to the sequence of PCR primer Ppa1r (SEQ ID NO:10) as shown in FIGS. 1 and 2A. More specifically, the 3' tail of SEQ ID NO:2 generated by PCR with primers Ppa1fNcoI (SEQ ID NO:13) and Ppa1r (SEQ ID NO:10) is identical to the 5' tail of SEQ ID NO:3 generated by PCR with primers Ppa8af7 (SEQ ID NO:11) and Ppa5ar1 (SEQ ID NO:8) as previously described. More specifically still, bases 218-250 of SEQ ID NO:2 are complementary to bases 1-33 of the complementary strand of SEQ ID NO:3. The double-stranded DNA comprising SEQ ID NO:2 and SEQ ID NO:3 were dissociated, annealed and elongated and then amplified by PCR using the PCR primers Ppa1fNcoI (SEQ ID NO:13) and Ppa5ar1 (SEQ ID NO:8) to generate a 1,089 bp PCR product comprising the cap1 promoter joined to the 3' flanking region of the cap5 promoter. The 1,089 bp PCR product is identified as SEQ ID NO:4. This 1,089 bp PCR product was ligated into pGEM T-vector (Promega, Madison, Wis.) and verified by sequencing.

DNA comprising SEQ ID NO:4 as ligated into pGEM T-vector was digested with the restriction enzymes NcoI and BamHI and purified according to standard techniques. (2)

DNA comprising SEQ ID NO:1 was generated by PCR. The PCR product was ligated into pGEM T-vector (Promega, Madison, Wis.) and verified by sequencing. The vector with the SEQ ID NO:1 insert was digested with restriction enzymes EcoRI and NcoI and purified according to standard techniques. (2)

EcoRI and NcoI digested DNA comprising SEQ ID NO:1 and NcoI and BamHI digested DNA comprising SEQ ID NO:4 were ligated such that the resulting DNA of the ligation comprised a 5' flanking region of the cap5 promoter ligated to a cap1 promoter that is operably linked to a 3' flanking region of the cap5 promoter as shown in FIG. 2. This DNA sequence is the modified 5' control region and is 1,858 bp in length as identified by SEQ ID NO:5. The modified 5' control region was verified by sequencing.

The shuttle vector pCL10 was digested with EcoRI and BamHI. The DNA comprising SEQ ID NO:5 that comprised DNA digested with EcoRI and BamHI restriction enzymes was purified and ligated into digested pCL10 as shown in FIG. 4. The resulting plasmid is a pCL10-modified 5' control region plasmid. pCL10 has been previously described. (3)

In various embodiments of the present invention, the pCL10-modified 5' control region plasmid may be introduced into a first host bacterial strain such as, for example, RN4220. The plasmid may be transferred via transduction from the first host bacterial strain to a second host bacterial strain such as, for example, *S. aureus* strain Reynolds.

In various embodiments of the present invention, electroporation may be used to introduce plasmids into *S. aureus*. Electroporation may be carried out by the following procedure:

1. Culture *S. aureus* strain RN4220 in sterile Trypticase Soy Broth ("TSB") overnight at 37° C. with agitation at approximately 225 revolutions per minute ("RPM"). Dilute the overnight culture 1:100 in TSB and incubate at 37° C. with agitation at approximately 225 RPM until the optical density at 660 nanometers ("$OD_{660}$") is in the range of approximately 0.3 to approximately 0.8 absorbance units. In various embodiments of the present invention, it may take approximately 2 hours and 10 minutes for the culture of RN4220 to reach an $OD_{660}$ of 0.32.

2. The culture may then be centrifuged at 10,000 RPM for 10 minutes to pellet the cells. The cell pellet may be resuspended in 0.8× volume of filter-sterilized 500 millimolar sucrose solution made from ultra-pure grade sucrose. The resuspended cells may be incubated on ice for approximately 30 minutes.

3. The resuspended cells may be centrifuged at 10,000 RPM for 10 minutes, the supernatant removed and the cells resuspended in 0.5× volume of filter-sterilized 500 millimolar sucrose solution made from ultra-pure grade sucrose. The resuspended cells may be incubated on ice for approximately 30 minutes.

4. The resuspended cells may be centrifuged at 10,000 RPM for 10 minutes, the supernatant removed and the cells resuspended in 0.01× volume of filter-sterilized 500 millimolar sucrose solution made from ultra-pure grade sucrose.

5. The resuspended competent cells may then be frozen in 125 µl aliquots in Eppendorf tubes on EtOH/dry-ice and subsequently stored at −70° C., or the competent cells may be used immediately for transformations.

6. Approximately 40 µl of the competent cells and 2 µl of plasmid DNA (approximately 0.5 µg/µl) may be added to a 0.2 cm electroporation cuvette. The mixture may be forced to the bottom by a quick shake.

7. The competent cells may be transformed by subjecting the electroporation cuvette containing the competent cells and the DNA to electroporation at 25 μF, 2.5 KV, and approximately 100Ω, approximately 200Ω, approximately 300Ω or approximately 400Ω.

8. Immediately after electroporation, approximately 250 μl TSB may be added to the cuvette. The cells may be withdrawn by a pipette. The cells may be introduced to agar plates comprising selective medium and incubated overnight at 37° C.

In various embodiments of the present invention, transduction of a recipient strain may be carried out with bacteriophage. The bacteriophage used in the transduction may be prepared as follows:

1. A host strain may be cultured overnight at 37° C. with agitation at approximately 225 RPM in appropriate selective medium. In various embodiments, the host strain may be RN4220 which has been transformed by electroporation with the pCL10-modified 5' control region plasmid. The overnight culture may be diluted 1:10 into 100 milliliters of TSB to make a new culture.
2. Incubate the new culture at 37° C. with agitation at approximately 225 RPM for approximately 1 hour 15 minutes to approximately 1 hour 30 minutes.
3. Four milliliters of 10 mg/ml $CaCl_2$ may be added to the new culture.
4. Bacteriophage may be added to the new culture at a Multiplicity of Infection ("MOI") of approximately 0.1. In various embodiments, the bacteriophage may be bacteriophage 52A.
5. The bacteriophage-infected new culture may be incubated at room temperature (approximately 25° C.) for approximately 30 minutes.
6. The bacteriophage-infected new culture may be agitated slowly at approximately 2 to approximately 3 hours at 30° C. The bacteriophage-infected new culture may be mixed and incubated overnight.
7. The cell debris may be pelleted by centrifugation and the supernatant purified by filter-sterilization. The filter-sterilized supernatant or lysate may contain bacteriophage comprising the pCL10-modified 5' control region plasmid.
8. The resulting filter-sterilized bacteriophage preparation may be tittered by serial dilution of the bacteriophage lysate in phage buffer. To each 0.1 milliliter of serially diluted bacteriophage lysate, add 0.2 milliliters sterile $CaCl_2$ (10 mg/ml), 0.2 milliliters of an appropriate bacterial strain, 4.5 ml soft agar (0.5% agar of Trypticase Soy Agar) and plate.
9. The plates may be incubated at 37° C. from approximately 6 hours to approximately 24 hours or alternatively until clear plaques are visible against a hazy lawn of bacteria. Bacteriophage titers may be obtained by counting the plaques present on plates and accounting for the appropriate dilution factor.
10. Phage buffer may be prepared as follows: Combine 6.47 grams of beta-glycerol phosphate, 0.12 grams of $MgSO_4 \cdot 7H_2O$, 2.4 grams NaCl, 0.5 grams gelatin, and 477.5 milliliters of $H_2O$. Autoclave the solution. Add 22.5 milliliters of cool, sterile 10 mg/ml $CaCl_2$.

In various embodiments of the present invention, transduction of a recipient strain such as, for example, S. aureus strain Reynolds, may be carried out with bacteriophage such as, for example, bacteriophage 52A, according to the following procedure:

1. The recipient strain may be cultured in 3 milliliters of TSB overnight at 37° C. with agitation at approximately 225 RPM.
2. Approximately 1 milliliter of the overnight culture may be used to inoculate 100 milliliters of fresh TSB to make a new recipient culture.
3. The new recipient culture may be incubated at 37° C. with agitation at approximately 225 RPM until about $5 \times 10^7$ to about $1 \times 10^8$ colony forming units per milliliter ("cfu/ml") is obtained. The $OD_{660}$ of the culture should be approximately 0.1 within about 1 hour 15 minutes to about 1 hour 30 minutes.
4. The cultured cells may be pelleted by centrifugation at 10,000 RPM for approximately 5 minutes or approximately 10 minutes or such time as is necessary.
5. The cells may be washed with approximately 5 to 10 milliliters of TSB and pelleted by centrifugation.
6. The cells may be resuspended in 1 milliliter of TSB.
7. An aliquot of 0.1 milliters of the resuspended cells may be removed for a total plate count and another 0.1 milliliter aliquot may be removed for plating to observe spontaneous mutants on selective agar.
8. To the remaining 0.8 milliliter, 0.1 milliliter of 10 mg/ml $CaCl_2$ may be added.
9. Bacteriophage may be added to the recipient cells to a multiplicity of infection of approximately 0.1 to approximately 1.0. For chromosomal markers, 0.8 ml phage lysate and 0.2 ml of 10 mg/ml $CaCl_2$ may be used.
10. The cells may be incubated at room temperature for approximately 10 minutes or such time as is necessary for adsorption of the phage to the cells.
11. In some instances it may be necessary to add 1 milliliter of cold 0.02 molar sodium citrate. This step is not required if bacteriophage 52A is utilized.
12. The cells may be incubated at 30° C. for 35 minutes without agitation, such as, for example, in a 30° C. water bath.
13. The cells may be diluted in 10 milliliters TSB, pelleted by centrifugation and resuspended in 10 milliliters TSB. The cells may be incubated at 37° C. for about 1 hour at approximately 225 RPM.
14. The cells may be pelleted by centrifugation and resuspended in about 1 milliliter of TSB. A portion of the resuspended cells such as, for example, 0.1 milliliters may be plated to a selective agar plate.
15. The selective agar plates may be incubated at 37° C. for approximately 24 hours to approximately 48 hours. Colonies, some of which may be transduced colonies, may form that are distinct from a background haze. In some instances, transductants may be visible in approximately 24 hours.

In various embodiments of the present invention, the pCL10-modified 5' control region plasmid is introduced into strain RN4220 bacteria by electroporation. In various embodiments of the present invention, the pCL10-modified 5' control region plasmid is introduced into S. aureus strain Reynolds via bacteriophage transduction. Furthermore, he 5' flanking region of the caps promoter and the 3' flanking region of the cap5 promoter which are part of the modified 5' control region are homologous to sequences of the S. aureus strain Reynolds genomic DNA. During replication of S. aureus strain Reynolds which has been transduced with the plasmid DNA comprising the modified 5' control region, the modified 5' control region may be integrated into the genomic DNA of S. aureus by homologous recombination. The homologous recombination event may occur such that the cap5 promoter sequence within the S. aureus genome is replaced by the cap1 promoter sequence encoded within the modified 5' control region of the plasmid. The resulting strain of S. aureus comprises a cap5 operon controlled by a constitutive promoter. Further, the resulting strain comprises a constitutive promoter operably linked to a cap5 operon. Further still, the resulting strain comprises a cap1 promoter operably linked to a cap5 operon. The DNA sequence of the constitutive promoter operably linked to the cap5 operon has been verified by sequencing. The resulting strain is CYL1892.

In various embodiments of the present invention, a strain of *Staphylococcus aureus* of the present invention comprises a DNA sequence comprising the cap1 promoter operably linked to the genes of the cap5 operon wherein the genes of the cap5 operon comprise the genes cap5A through cap5P as listed in SEQ ID NO:6. In various embodiments of the present invention, a strain of *Staphylococcus aureus* of the present invention comprises a DNA sequence comprising the cap1 promoter operably linked to the genes of the cap5 operon wherein the genes of the cap5 operon comprise the genes cap5A through cap5O as listed in SEQ ID NO:7.

The following examples are further illustrative of the present invention, but it is understood that the invention is not limited thereto.

Figure 5:
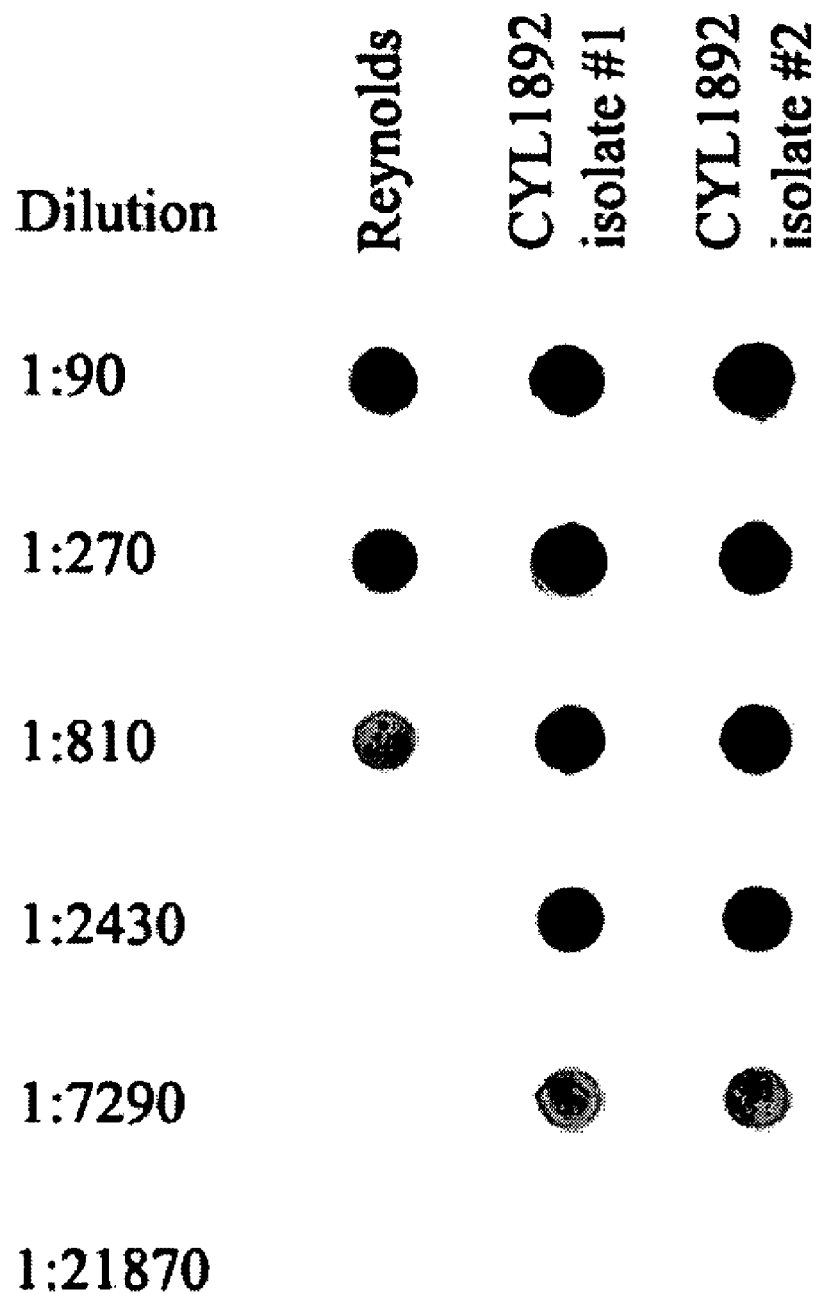
FIG. 5 illustrates differences in type 5 capsular polysaccharide production from a liquid culture of *Staphylococcus aureus* strain Reynolds and two independent liquid cultures of *Staphylococcus aureus* strain CYL1892 as detected by immuno-dot blotting.

FIG. 5 illustrates type 5 capsular polysaccharide production in one culture of *S. aureus* strain Reynolds and two independent cultures of *S. aureus* strain CYL1892. Cell-associated capsular polysaccharide may be dissociated as follows:

1. *S. aureus* strain Reynolds and *S. aureus* strain CYL1892 may be cultured overnight in TSB at 37° C. with agitation at approximately 225 RPM.
2. The $OD_{660}$ of 1:10 dilutions of overnight cultures of cultures of *S. aureus* strain Reynolds and *S. aureus* strain CYL1892 may be determined.
3. Cells from 1 milliliter of each culture may be pelleted by centrifugation and the cells from each sample may be resuspended in 10 µl of 1× Phosphate buffered saline ("PBS") per $OD_{660}$ unit.
4. One µl of Lysostaphin (10 mg/ml) may be added to the resuspended cells and the mixture incubated at 37° C. for approximately 15 minutes.
5. Subsequently, 0.4 µl of DNase I (75 ug/µl) may be added to the mixture and further incubated at 37° C. for approximately 15 minutes.
6. Cell debris may be pelleted by centrifugation. To the supernatant, 1 µl of Proteinase K (10 mg/ml) may be added and the mixture further incubated at 37° C. for approximately 30 minutes. Another 1 µl of Proteinase K (10 mg/ml) may be added to the previous mixture and said mixture further incubated at 37° C. for approximately 30 minutes.
7. The mixture may be heated at 75° C. for approximately 10 minutes and centrifuged to remove debris. The supernatant may contain capsular polysaccharide for further analysis.

Immuno-dot blotting may be performed according to the following procedure:

1. A vacuum dot-blot apparatus may be prepared by cleaning the apparatus including the manifold of the apparatus with distilled water.
2. A section of nitrocellulose paper may be soaked in 1× PBS for 10 minutes.
3. The wet nitrocellulose paper may be placed on the manifold and unnecessary air should be removed. The apparatus should be further assembled as necessary.
4. All sample chambers may be washed with 1× PBS by applying 1× PBS to each chamber and removing the 1× PBS by vacuum. The sample chambers should be re-filled with 1× PBS.
5. Capsule samples may be serially diluted approximately two-fold to three-fold in approximately 30 µl to approximately 50 µl of 1× PBS.
6. Vacuum pressure should be used to remove the 1× PBS in the sample chambers. After removal, the vacuum pressure should be discontinued.
7. Serially diluted samples may be applied to the sample chambers. Gentle vacuum pressure should be applied. After all fluid in the sample chamber has been removed by vacuum, each sample chamber may be washed with 1 milliliter of 1× PBS by application of the 1× PBS to the sample chambers and removal by vacuum. Vacuum pressure may be applied for approximately 5 or more minutes to dry the nitrocellulose paper.
8. The nitrocellulose paper may be removed from the vacuum dot blot apparatus and placed into a container.
9. The nitrocellulose paper in the container may be incubated in approximately 10 milliliters of TS-skim milk at room temperature for approximately 1 hour with mild agitation. The container may be covered.
10. The nitrocellulose paper may be washed twice with approximately 15 milliliters of TS per wash.
11. The nitrocellulose paper may be incubated in 10 milliliters of TS-skim milk comprising anti-type 5 capsule primary rabbit antibody (kindly provided by Dr. Ali Fattom of NABI in Rockville, Md.) at room temperature for approximately 1 hour with mild agitation. The incubation may occur in a covered container.
12. The nitrocellulose paper may be washed three times with approximately 15 milliliters of TS per wash.
13. The nitrocellulose paper may be incubated in 10 milliliters of TS-skim milk comprising horseradish-peroxidase conjugated goat anti-rabbit at room temperature for approximately 1 hour with mild agitation. The incubation may occur in a covered container.
14. The nitrocellulose paper may be washed twice with approximately 15 milliliters of TS per wash. The nitrocellulose paper may be exposed to color development reagent.

10× PBS (pH 7.5) comprises the-following: 0.06 grams of $KH_2PO_4$, 1.85 grams of $Na_2HPO_4$, 7.65 grams of NaCl and $H_2O$ to 100 milliliters. 10× TS comprises the following: 0.1M Tris.Cl (pH 7.5) and 1.5M NaCl. TS-skim milk comprises the following: 1× TS and 5% skim milk freshly prepared for each use and slightly warmed in a microwave oven.

Color developing reagent comprises the following: i) 12 mg HRP color developing reagent (BioRad) in 4 milliliters of Methanol; and ii) 0.012 milliliters of 30% $H_2O_2$ in 20 milliliters of TS. Parts i) and ii) of the color developing reagent should be mixed immediately prior to application.

Quantitation of type 5 capsular polysaccharide production illustrated in FIG. 5 was performed using a Kodak Molecular Image System. The results indicated that strain CYL1892 produced about 11.5 fold more type 5 capsular polysaccharide than strain Reynolds. In various embodiments of the present invention, a *Staphylococcus aureus* strain comprising a constitutive promoter operably linked to a cap5 operon may produce about 5 fold more type 5 capsular polysaccharide, about 9 fold more type 5 capsular polysaccharide, or about 11.5 fold more type 5 capsular polysaccharide than strain Reynolds.

Figure 6:
FIG. 6 illustrates differences in morphology between *Staphylococcus aureus* strain Reynolds (left) and *Staphylococcus aureus* strain CYL1892 (right).

The overproduction of type 5 capsular polysaccharide in CYL1892 is demonstrated on solid agar plates. FIG. 6 compares the gross morphology of *S. aureus* strain Reynolds (left) and *S. aureus* strain CYL1892 (right) after approximately 40 hours of growth at 30° C. on solid Trypticase Soy Agar plates. As shown in FIG. 6, CYL1892 has a larger colony size and more mucoid appearance on Trypticase Soy Agar plates than the strain Reynolds. Accepting that mucoid appearance is indicative of capsule production, these results indicate that the engineered strain CYL1892 constitutively produces more type 5 capsular polysaccharide than the wild-type strain.

In various embodiments of the present invention, PCR may be carried out using the Advantage HF-2 PCR kit from Stratagene according to the manufacturer's instructions. The PCR may comprise the following protocol:
1. 95° C. for 30 seconds;
2. 95° C. for 60 seconds;
3. 60° C. for 180 seconds;
4. Repeat parts 2 and 3 for 30 cycles; and
5. 60° C. for 300 seconds.

In various embodiments of the present invention, plasmid DNA may be purified with a plasmid purification kit (Qiagen, Inc., Chatsworth, Calif.). PCR products may be separated by agarose gel elctrophoresis and purified by a PCR product purification kit (Qiagen, Inc., Chatsworth, Calif.). Bulk chromosomal DNA from S. aureus may be purified with a chromosomal DNA purification kit (Promega, Madison, Wis.). PCR amplification may be carried out with the Advantage cDNA PCR kit (Clontech, Palo Alto, Calif.) or the Advantage HF-2 PCR kit (Stratagene, La Jolla, Calif.). Unless otherwise described but without being limited thereto, standard DNA manipulations and other molecular biology techniques may be performed as described by Sambrook, et al. (2).

Genomic DNA from S. aureus strain Reynolds, a type 5 capsular polysaccharide producing strain containing the cap5 locus, was used as the template for the 5' flanking region of the cap5 promoter and the 3' flanking region of the cap5 promoter. Genomic DNA from S. aureus strain M, a type 1 capsular polysaccharide producing strain containing the cap1 locus, was used as the template for the cap1 promoter.

S. aureus RN4220 was used as the recipient in electroporations of the pCL10-modified 5' control region plasmid.

Bacteriophage 52A was used to transduce pCL10-modified 5' control region plasmid from RN4220 to S. aureus strain Reynolds.

S. aureus strain Reynolds, a type 5 capsular polysaccharide producing strain containing the cap5 locus, was used as the parent strain for constructing the type 5 capsular polysaccharide overproducing strain, CYL1892. S. aureus strain Reynolds was transduced with bacteriophage comprising the pCL10-modified 5' control region plasmid. S. aureus strain CYL1892 resulted from homologous recombination of the pCL10-modified 5' control region plasmid with S. aureus strain Reynolds genomic DNA.

Escherichia coli strain XL1-Blue was used as a host strain for plasmid constructions.

S. aureus strains were cultured in Trypticase soy medium (Difco Laboratories, Detroit, Mich.). E. coli strains were cultured in Luria-Bertani medium (Difco Laboratories). Where applicable, bacteria were cultured on agar plates containing the appropriate aforementioned media and 0.5% agar.

In various embodiments of the present invention, DNA sequences are listed as single-stranded DNA sequences. These sequences should not be construed to be limited to merely the single strand of DNA but should be construed to encompass a complementary strand where applicable.

All references cited in this specification are hereby incorporated by reference in their entirety. The discussion of the references herein is intended merely to summarize the assertions made by their authors and no admission is made that any reference constitutes prior art relevant to patentability. Applicant reserves the right to challenge the accuracy and pertinence of the cited references.

As various changes could be made in the above methods and compositions without departing from the scope of the invention, it is intended that all matter contained in the above description be interpreted as illustrative and not in a limiting sense. Unless explicitly stated to recite activities that have been done (i.e., using the past tense), illustrations and examples are not intended to be a representation that given embodiments of this invention have, or have not, been performed.

REFERENCES

1. Higuchi, R. 1989. Using PCR to engineer DNA, p. 61-70. In H. A. Erlich (ed.), PCR technology. Stockton Press, New York, N.Y.
2. Sambrook, J., E. F. Fritsch, and T. Maniatis. 1989. Molecular cloning: a laboratory manual, 2nd ed. Cold Spring Harbor Laboratory, Cold Spring Harbor, N.Y.
3. S. Sau, J. Sun and C. Y. Lee. 1997. Molecular characterization and transcriptional analysis of type 8 capsule genes in Staphylococcus aureus. J. Bacteriol. 179:1614-1621.

What is claimed is:

1. A strain of *Staphylococcus aureus* comprising a constitutive promoter wherein said constitutive promoter is operably linked to a cap5 operon wherein said constitutive promoter is the cap1 promoter of *Staphylococcus aureus* strain M comprising SEQ ID NO 2.

2. A strain of *Staphylococcus aureus* comprising a constitutive promoter wherein said constitutive promoter is operably linked to a cap5 operon wherein said constitutive promoter is the cap1 promoter of *Staphylococcus aureus* strain M comprising SEQ ID NO 2, and wherein the cap1 promoter and cap5 operon comprise the deoxyribonucleic acid sequence SEQ ID NO: 6.

3. The strain of *Staphylococcus aureus* of claim 1, wherein type 5 capsular polysaccharide production is five-fold greater than *Staphylococcus aureus* strain Reynolds.

4. The strain of *Staphylococcus aureus* of claim 1, wherein type 5 capsular polysaccharide production is nine-fold greater than *Staphylococcus aureus* strain Reynolds.

5. The strain of *Staphylococcus aureus* of claim 1, wherein type 5 capsular polysaccharide production is 11.5-fold greater than *Staphylococcus aureus* strain Reynolds.

6. An isolated deoxyribonucleic acid sequence comprising SEQ ID NO 5.

7. An isolated deoxyribonucleic acid sequence comprising SEQ ID NO 6.

* * * * *

UNITED STATES PATENT AND TRADEMARK OFFICE
CERTIFICATE OF CORRECTION

PATENT NO.         : 7,521,221 B2                                              Page 1 of 1
APPLICATION NO.    : 11/285700
DATED              : April 21, 2009
INVENTOR(S)        : Chia Y. Lee and Thanh T. Luong It is certified that error appears in the above-identified patent and that said Letters Patent is hereby corrected as shown below:

On the title page item (73),
In the Assignee name, "Arknasas" should read --Arkansas--

Signed and Sealed this

Third Day of November, 2009

David J. Kappos
*Director of the United States Patent and Trademark Office*

SEQUENCE LISTING

<160> NUMBER OF SEQ ID NOS: 13

<210> SEQ ID NO 1
<211> LENGTH: 778
<212> TYPE: DNA
<213> ORGANISM: Staphylococcus aureus

<400> SEQUENCE: 1

```
gaattcgagt ctacaagcga ttaaattgac gttcgaatat ttaaaatcat ctgttgaaaa      60
gggtgataaa gtttcaagag agaaaatgca taacgcatca actttggctg gtatggcatt     120
tgcaaatgca ttcttaggca ttgcacactc aattgcacat aaaattggtg gcgaatatgg     180
tattccgcat ggtagagcga atgcgatatt actaccgcat attatccgtt ataatgccaa     240
agacccgcaa aaacatgcat tattccctaa atatgagttc ttcagagcag atacagatta     300
tgcagatatt gccaaattct taggattaaa agggaatacg acagaagcac tcgtagaatc     360
attagctaaa gctgtctacg aattaggtca atcagtcgga attgaaatga atttgaaatc     420
```

```
acaaggtgtg tctgaagaag aattaaatga atcaattgat agaatggcag agctcgcatt    480
tgaagatcaa tgtacaactg ctaatcctaa agaagcacta atcagtgaaa tcaaagatat    540
cattcaaaca tcatatgatt ataagcaata atctatctga taataatcat ataactcacc    600
tgaaattaca aaagtaaaaa atgccacata aactttaagt cgataatcat tttacggtta    660
tcggctttta tttattgcca aatcttcaga gatacaaact agacaatcat tttttttaaat   720 aaagaaaata ttaagattga tactcatttc gcaaactatt actactttag agccatgg     778

<210> SEQ ID NO 2
<211> LENGTH: 250
<212> TYPE: DNA
<213> ORGANISM: Staphylococcus aureus

<400> SEQUENCE: 2
cggccatggc cacagtataa attatatcag tatgcttata taattttga aatctttaaa     60 caaatgaagt aataattgag aaaagtgtag ttaaattatt tttcttgaaa ttatttgtta   120
catagcattt cgatgtaaaa ttcactttt ataagtaaat ttaaaaagag tttgcaaaat    180
atacagggga ttatatataa tggaaaacaa gaaaggaaaa taggaggttt atatggaaag   240
tacattagaa                                                          250

<210> SEQ ID NO 3
<211> LENGTH: 872
<212> TYPE: DNA
<213> ORGANISM: Staphylococcus aureus

<400> SEQUENCE: 3
aaataggagg tttatatgga aagtacatta gaattaacaa aaattaaaga agtattacaa     60
aaaaacttga agatttttaat tattttaccg ctattatttt taattattag cgctattgtt  120
acatttttcg tcttatcacc taaatatcaa gctaatactc aaatcttagt gaatcaaact   180
aagggtgaca atcctcagtt tatggcacaa gaggttcaaa gtaatattca acttgtaaat   240
acgtataaag aaattgttaa aagtcctaga attttagatg aggtgtcaaa ggacttaaat   300
gataagtatt caccatctaa attgtcgagt atgttgacaa ttacaaacca agaaaatacg   360
caacttatca acatccaagt taaaagtggt cataaacaag attcggaaaa aattgcgaat   420
agcttcgcta aagttacaag taaacaaatt ccgaagatta tgagtgtgga taacgtatca   480
attttatcta aagcagacgg tacagcagtt aaagtcgcac caaaaactgt agtgaatcta   540
atcggtgcat tcttttagg attagttgtc gcgcttatat atatcttctt caaagtaatt   600 tcgataagc gaattaaaga tgaagaagat gtagagaaag aattaggatt gcctgtattg   660
ggttcaattc aaaaatttaa ttaaggatgg ttgctactta tgtcaaaaaa ggaaaatacg   720
acaacaacac tatttgtata tgaaaaacca aaatcaacaa ttagtgaaaa gtttcgaggt   780
atacgttcaa acatcatgtt tcaaaagca aatggtgaag taaagcgctt attggttact   840
tctgaaaagc ctggtgcagg taaaagggat cc                                 872

<210> SEQ ID NO 4
<211> LENGTH: 1089
<212> TYPE: DNA
<213> ORGANISM: Staphylococcus aureus

<400> SEQUENCE: 4
cggccatggc cacagtataa attatatcag tatgcttata taattttga aatctttaaa    60
```

-continued

```
caaatgaagt aataattgag aaaagtgtag ttaaattatt tttcttgaaa ttatttgtta        120
catagcattt cgatgtaaaa ttcactttt ataagtaaat ttaaaaagag tttgcaaaat         180
atacagggga ttatatataa tggaaaacaa gaaaggaaaa taggaggttt atatggaaag       240
tacattagaa ttaacaaaaa ttaaagaagt attacaaaaa aacttgaaga ttttaattat        300
tttaccgcta ttattttaa ttattagcgc tattgttaca tttttcgtct tatcacctaa        360
atatcaagct aatactcaaa tcttagtgaa tcaaactaag ggtgacaatc ctcagtttat       420
ggcacaagag gttcaaagta atattcaact tgtaaatacg tataagaaa ttgttaaaag        480 tcctagaatt ttagatgagg tgtcaaagga cttaaatgat aagtattcac catctaaatt       540
gtcgagtatg ttgacaatta caaccaaga aaatacgcaa cttatcaaca tccaagttaa       600
aagtggtcat aaacaagatt cggaaaaaat tgcgaatagc ttcgctaaag ttacaagtaa       660
acaaattccg aagattatga gtgtggataa cgtatcaatt ttatctaaag cagacggtac       720
agcagttaaa gtcgcaccaa aaactgtagt gaatctaatc ggtgcattct ttttaggatt      780
agttgtcgcg cttatatata tcttcttcaa agtaattttc gataagcgaa ttaaagatga     840
agaagatgta gagaaagaat taggattgcc tgtattgggt tcaattcaaa aatttaatta      900
aggatggttg ctacttatgt caaaaaagga aaatacgaca caacactat ttgtatatga      960 aaaccaaaa tcaacaatta gtgaaaagtt tcgaggtata cgttcaaaca tcatgttttc      1020
aaaagcaaat ggtgaagtaa agcgcttatt ggttacttct gaaaagcctg gtgcaggtaa    1080
aagggatcc                                                              1089
```

<210> SEQ ID NO 5
<211> LENGTH: 1858
<212> TYPE: DNA
<213> ORGANISM: Staphylococcus aureus

<400> SEQUENCE: 5

```
gaattcgagt ctacaagcga ttaaattgac gttcgaatat ttaaaatcat ctgttgaaaa         60
gggtgataaa gtttcaagag agaaaatgca taacgcatca actttggctg gtatggcatt       120
tgcaaatgca ttcttaggca ttgcacactc aattgcacat aaaattggtg gcgaatatgg       180
tattccgcat ggtagagcga atgcgatatt actaccgcat attatccgtt ataatgccaa       240
agacccgcaa aaacatgcat tattccctaa atatgagttc ttcagagcag atacagatta       300
tgcagatatt gccaaattct taggattaaa agggaatacg acagaagcac tcgtagaatc       360
attagctaaa gctgtctacg aattaggtca atcagtcgga attgaaatga atttgaaatc       420
acaaggtgtg tctgaagaag aattaaatga atcaattgat agaatggcag agctcgcatt       480
tgaagatcaa tgtacaactg ctaatcctaa agaagcacta atcagtgaaa tcaaagatat       540
cattcaaaca tcatatgatt ataagcaata atctatctga taataatcat ataactcacc       600
tgaaattaca aaagtaaaaa atgccacata aactttaagt cgataatcat tttacggtta       660
tcggctttta tttattgcca aatcttcaga gatacaaact agacaatcat tttttaaat       720 aaagaaaata ttaagattga tactcatttc gcaaactatt actactttag agccatggcc       780
acagtataaa ttatatcagt atgcttatat aattttgaa atctttaaac aaatgaagta       840
ataattgaga aaagtgtagt taaattattt ttccttgaaa tatttgttac atagcatttc      900
gatgtaaaat tcacttttta taagtaaatt taaaaagagt ttgcaaaata tacaggggat      960
tatatataat ggaaaacaag aaaggaaaat aggaggttta tatggaaagt acattagaat    1020
taacaaaaat taaagaagta ttacaaaaaa acttgaagat tttaattatt ttaccgctat    1080
```

```
tatttttaat tattagcgct attgttacat ttttcgtctt atcacctaaa tatcaagcta   1140
atactcaaat cttagtgaat caaactaagg gtgacaatcc tcagtttatg cacaagagg    1200 ttcaaagtaa tattcaactt gtaaatacgt ataaagaaat tgttaaaagt cctagaattt   1260
tagatgaggt gtcaaaggac ttaaatgata agtattcacc atctaaattg tcgagtatgt   1320
tgacaattac aaaccaagaa aatacgcaac ttatcaacat ccaagttaaa agtggtcata   1380
aacaagattc ggaaaaaatt gcgaatagct tcgctaaagt tacaagtaaa caaattccga   1440
agattatgag tgtggataac gtatcaattt tatctaaagc agacggtaca gcagttaaag   1500
tcgcaccaaa aactgtagtg aatctaatcg gtgcattctt tttaggatta gttgtcgcgc   1560
ttatatatat cttcttcaaa gtaattttcg ataagcgaat taaagatgaa gaagatgtag   1620
agaaagaatt aggattgcct gtattgggtt caattcaaaa atttaattaa ggatggttgc   1680
tacttatgtc aaaaaggaa aatacgacaa caacactatt tgtatatgaa aaaccaaaat    1740
caacaattag tgaaaagttt cgaggtatac gttcaaacat catgttttca aaagcaaatg   1800
gtgaagtaaa gcgcttattg gttacttctg aaaagcctgg tgcaggtaaa agggatcc    1858
```

<210> SEQ ID NO 6
<211> LENGTH: 17566
<212> TYPE: DNA
<213> ORGANISM: Staphylococcus aureus

<400> SEQUENCE: 6

```
gagtctacaa gcgattaaat tgacgttcga atatttaaaa tcatctgttg aaaagggtga    60
taaagtttca agagagaaaa tgcataacgc atcaactttg gctggtatgg catttgcaaa   120
tgcattctta ggcattgcac actcaattgc acataaaatt ggtggcgaat atggtattcc   180
gcatggtaga gcgaatgcga tattactacc gcatattatc cgttataatg ccaaagaccc   240
gcaaaaacat gcattattcc ctaaatatga gttcttcaga gcagatacag attatgcaga   300
tattgccaaa ttcttaggat taaaagggaa tacgacagaa gcactcgtag aatcattagc   360
taaagctgtc tacgaattag gtcaatcagt cggaattgaa atgaatttga atcacaagg    420 tgtgtctgaa gaagaattaa atgaatcaat tgatagaatg gcagagctcg catttgaaga   480
tcaatgtaca actgctaatc ctaaagaagc actaatcagt gaaatcaaag atatcattca   540
aacatcatat gattataagc aataatctat ctgataataa tcatataact cacctgaaat   600
tacaaaagta aaaaatgcca cataaacttt aagtcgataa tcattttacg gttatcggct   660
tttatttatt gccaaatctt cagagataca aactagacaa tcattttttt aaataaagaa   720
aatattaaga ttgatactca tttcgcaaac tattactact ttagagccat ggccacagta   780
taaattatat cagtatgctt atataatttt tgaaatcttt aaacaaatga agtaataatt   840
gagaaaagtg tagttaaatt attttttcttg aaattatttg ttacatagca tttcgatgta   900
aaattcactt tttataagta aatttaaaaa gagtttgcaa aatatacagg ggattatata   960
taatggaaaa caagaaagga aaataggagg tttatatgga agtacatta gaattaacaa    1020 aaattaaaga agtattacaa aaaaacttga agattttaat tattttaccg ctattatttt   1080
taattattag cgctattgtt acatttttcg tcttatcacc taaatatcaa gctaatactc   1140
aaatcttagt gaatcaaact aagggtgaca atcctcagtt tatggcacaa gaggttcaaa   1200
gtaatattca acttgtaaat acgtataaag aaattgttaa aagtcctaga attttagatg   1260
aggtgtcaaa ggacttaaat gataagtatt caccatctaa attgtcgagt atgttgacaa   1320
```

```
ttacaaacca agaaaatacg caacttatca acatccaagt taaaagtggt cataaacaag    1380
attcggaaaa aattgcgaat agcttcgcta aagttacaag taaacaaatt ccgaagatta    1440
tgagtgtgga taacgtatca attttatcta aagcagacgg tacagcagtt aaagtcgcac    1500
caaaaactgt agtgaatcta atcggtgcat tcttttagg attagttgtc gcgcttatat     1560
atatcttctt caaagtaatt ttcgataagc gaattaaaga tgaagaagat gtagagaaag    1620
aattaggatt gcctgtattg ggttcaattc aaaaatttaa ttaaggatgg ttgctactta    1680
tgtcaaaaaa ggaaaatacg acaacaacac tatttgtata tgaaaaccca aaatcaacaa    1740
ttagtgaaaa gtttcgaggt atacgttcaa acatcatgtt ttcaaaagca aatggtgaag    1800
taaagcgctt attggttact tctgaaaagc ctggtgcagg taaaagtaca gttgtatcga    1860
atgtagcgat tacttatgca caagcaggct ataagacatt agttattgat ggcgatatgc    1920
gtaagccaac acaaaactat atttttaatg agcaaaataa taatggacta tcaagcttaa    1980
tcattggtcg aacgactatg tcagaagcaa ttacgtcgac agaaattgaa aatttagatt    2040
tgctaacagc tggccctgta cctccaaatc catctgagtt aattgggtct gaaaggttca    2100
aagaattagt tgatctgttt aataaacgtt acgacattat tattgtcgat acaccgccag    2160
ttaatactgt gactgatgca caactatatg cgcgtgctat taaagatagt ctgttagtaa    2220
ttgatagtga aaaaaatgat aaaaatgaag ttaaaaaagc aaaagcactt atggaaaaag    2280
caggcagtaa cattctaggt gtcattttga acaagacaaa ggtcgataaa tcttctagtt    2340
attatcacta ttatggagat gaataagtat gattgatatt cataaccata tattgcctaa    2400
tatcgatgac ggtccgacaa atgaaacaga gatgatggat cttttaaaac aagcgacaac    2460
acaaggtgtt acagaaatca ttgtaacatc acatcactta catcctcgat ataccacacc    2520
tatagaaaaa gtgaaatcat gtttaaacca tattgaaagc ttagaggaag tacaagcact    2580
aaatctaaag ttttattatg gtcaggaaat aagaattacc gatcaaatcc ttaatgatat    2640
tgatcgaaaa gttattaccg gtattaatga ttcacgctat ttactaatag aatttccatc    2700
aaatgaagtt ccacactata ctgatcaatt attttcgaa ttacagagta aaggctttgt     2760
accgattatt gcacatccag agcgaaataa agcaataagt caaaaccttg acatactata    2820
cgatttaatt aacaaaggtg ctttaagtca agtgacaacg gcgtcattag cgggtatttc    2880
cggtaaaaaa attagaaaat tagcaattca aatgattgaa aacaatctga cacatttcat    2940
cggttcagat gcgcataaca cagaaatcag accgttctta atgaaagact tatttaatga    3000
taagaaatta cgtgattatt atgaagatat gaacggattt attagtaatg cgaagttagt    3060
tgttgatgat aaaaaaattc ctaaacgaat gccacaacaa gattataaac agaaaagatg    3120
gtttgggtta taaacagcaa atgagggggtt ttatggcaca tttatctgtg aaattgcggc    3180
ttttaatact agcattaatc gattcactga tagtgacatt tcagtattc gtaagttatt      3240 acattttaga accgtatttc aaaacatatt ctgtcaaatt attaatattg gcagctatat    3300
cactattcat atcgcatcat atttcagcat ttatttttaa tatgtatcat cgagcgtggg    3360
aatatgccag tgtgagtgaa ttgatttttaa ttgttaaagc tgtgacgaca tctatcgtta    3420
ttacgatggt ggtcgtgaca attgttacag gcaatagacc gtttttaga ttgtatttaa     3480 ttacttggat gatgcacttg attttaatag gtggctcaag gttattttgg cgtatttatc    3540
ggaaatacct tggaggtaag tcatttaata agaagccaac tttagttgtt ggtgctggtc    3600
aagcaggttc aatgctgatt agacaaatgt tgaaagtga cgaaatgaaa cttgaaccgg     3660
tattagcagt cgatgatgac gaacataaac gcaatatcac aattactgag ggtgtaaaag    3720
```

-continued

```
tccaaggtaa aattgcggat attccagaac tagtgaggaa atataagatt aaaaaaatca   3780
tcattgcaat tccaactatt ggtcaagagc gtttgaaaga aattaataat atttgccata   3840
tggatggcgt tgagttattg aaaatgccaa atatagaaga cgtcatgtct ggtgagttag   3900
aagtgaatca actgaaaaaa gttgaagtag aagatttact aggcagagat cctgttgaat   3960
tagatatgga tatgatatca aatgaattga cgaataaaac tattttagtt acgggtgcag   4020
gtggttcaat aggatcagaa atttgtagac aagtttgtaa tttctatcca gaacgtatta   4080
ttctacttgg ccatggtgaa aacagtattt atttaatcaa tcgtgaattg cgaaatcgct   4140
tcggaaaaaa tgttgatatc gttcctatta tagcggatgt gcaaaataga gcgcgtatgt   4200
ttgaaattat ggaaacgtat aaaccatacg cagtttatca tgcagcagca cacaagcacg   4260
tgccgttaat ggaagacaac cctgaagaag cagtacataa taatattta ggtacgaaaa   4320
atactgctga agctgctaaa aatgcagagg taaagaaatt cgttatgatt tctacggata   4380
aagccgttaa tccgcctaat gtcatgggag cttcaaagcg aattgcagaa atgattattc   4440
aaagtttaaa tgatgaaacg catcgaacaa attttgttgc agtgagattt ggtaatgtac   4500
ttggatcgag aggatctgtg attccacttt tcaaaagtca aattgaagaa ggtgggccag   4560
ttactgtgac acatcctgaa atgacacgtt actttatgac aattcctgaa gcttctagac   4620
tagttttgca ggcaggggca ttagcagaag gtggcgaagt atttgtgcta gatatgggag   4680
aaccagtgaa aattgtagat ttggcacgta atttaattaa gctaagtggt aaaaaagaag   4740
acgcatacg cattacttat acagggatta gacccggcga aaaaatgttt gaagagctta   4800
tgaataaaga tgaggttcat cctgaacaag tatttgaaaa aatttatcgt ggcaaagtac   4860
aacatatgaa atgtaatgaa gttgaagcga ttattcaaga catcgtcaat gactttagta   4920
aagaaaaaat tattaactat gccaatggca aaagggaga taattatgtt cgatgacaaa   4980
atttattaa ttactggggg cacaggatca ttcggtaatg ctgttatgaa acggttttta   5040
gattctaata ttaaagaaat tcgtattttt tcacgcgatg agaaaaaaca agatgacatt   5100
cgaaaaaaat ataataattc aaaattaaag ttctacattg gtgatgtgcg tgatagtcaa   5160
agtgtagaaa cagcaatgcg agatgttgat tacgtattcc atgcagcagc tttaaaacaa   5220
gtgccgtcat gtgaattctt tccagttgag gcagtgaaga caaatattat tggtacagaa   5280
aatgtcttac aaagtgctat tcatcaaaat gttaaaaaag tcatatgtttt atctacagat   5340
aaggcagcgt atcctattaa tgctatgggt atttcaaaag caatgatgga aaaagtattc   5400
gtagccaaat caagaaatat tcgtagtgaa caaacgctta tttgtggtac aagatacggt   5460
aatgtgatgg cttcaagagg atcagtaata cctttgttta tcgacaaaat caaagctgga   5520
gaacctttaa cgattacaga tcctgatatg acaagatttt taatgagctt agaagatgcg   5580
gtagaactag ttgttcatgc atttaagcat gcagagacag gagatattat ggttcaaaaa   5640
gcaccaagct caacggtagg ggatcttgcg accgcattat agaattgtt tgaagctgat   5700
aatgcaattg aaatcattgg tacgcgacat ggagagaaaa aagcagaaac attgttgacg   5760
agagaagaat acgcacaatg tgaagatatg ggtgattatt ttagagtgcc ggcagactcc   5820
agagatttaa attatagtaa ttatgttgaa accggtaacg aaaagattac gcaatcttat   5880
gaatataact ccgataatac acatatttta acggtggaag agataaaaga aaaacttttta   5940
acactgaat atgttagaaa cgaattgaat gattataaag cttcaatgag ataggagaga   6000
ttgacgttga atattgtaat tacaggagca aaaggttttg taggaaaaaa cttgaaagca   6060
```

```
gatttaacat caacgacaga tcatcatatt ttcgaagtac atcgacaaac taaagaggaa    6120
gaattagagt cagcattgtt gaaagcagac tttatcgtgc atttagcggg tgttaatcga    6180
cctgaacatg acaaagaatt cagcttagga aacgtgagtt atttagatca tgtacttgat    6240
atattaacta gaaatacgaa aaagccagcg atattattat cgtcttcaat acaagcaaca    6300
caagataatc cttatggtga gagtaagttg caagggaac agctattaag agagtatgcc     6360
gaagagtatg caatacggt ttatatttat cgctggccaa atttattcgg caagtggtgt     6420
aagccgaatt ataactcagt gatagcaaca ttttgttaca aaattgcacg taacgaagag    6480
attcaagtta atgatcggaa tgttaacta acgctaaact acgtggatga tatcgtcgct     6540
gaaataaagc gtgctattga aggaactcca acgattgaaa atggtgtacc tacagtacca    6600
aacgtattta aagtgacatt gggagaaatt gtagatttat tatacaagtt caaacagtca    6660
cgtctcgatc gaacattgcc gaaattagat aacttgtttg aaaaagattt gtatagtacg    6720
tatttaagct atctacctag tacagacttt agttatccct tacttatgaa tgtggatgat    6780
aggggttctt ttacagaatt tataaaaaca ccggatcgtg gtcaagtttc tgtaaatatt    6840
tctaaaccag gtattactaa aggtaatcac tggcaccata ctaaaaacga aaaatttcta    6900
gtcgtatcag gtaaaggggt aattcgtttt agacatgtta atgatgatga aatcattgaa    6960
tattacgttt ctggcgataa attagaagtt gtagacatac cagtaggata cacacataat    7020
attgaaaatt taggcgacac agatatggta actattatgt gggtgaatga aatgtttgat    7080
ccaaatcagc cagatacgta tttcttggag gtatagcgca tggaaaaact gaaattaatg    7140
acaatagttg gtacaaggcc tgaaatcatt cgtttatcat caacgattaa agcatgtgat    7200
caatatttta atcagatatt agtacacact ggtcaaaatt atgattatac attgaatcaa    7260
attttctttg atgatttgga attaagacaa ccggaccact acttagaggc agttggaagt    7320
aaccttggag aaacgatggg gaatattatt gcgaagacat atgacgtttt attacgcgaa    7380
caaccagatg cactttttaat tcttggtgat acaaatagtt gtttagcagc agtatctgct    7440
aaacgattaa agattcctgt gttccacatg gaagcgggta atagatgctt tgatcagaat    7500
gtacctgaag aaatcaatcg taaaattgtt gaccatgtca gtgatgtgaa tctaccttat    7560
acagaacata gcagacggta tttattagat gaaggcttca ataaagcgaa tatctttgtg    7620
acaggatcac cgatgacaga agtgatagaa gcgcatcgag ataaaattaa tcacagtgac    7680 gtttaaata aactaggatt agaaccgcaa caatacattt tagtatctgc gcatagagaa    7740
gagaatatcg ataatgaaaa gaattttaaa tcattaatga atgcgataaa tgatattgcc    7800
aaaaagtata aaatgcctgt gatttattca acgcatccaa gaagttggaa gaaaattgaa    7860
gaaagtaaat ttgaatttga tccattagtt aaacagttaa agccatttgg tttctttgat    7920
tataatgcat tgcaaaaaga tgcatttgtt gtgctatcag atagtggaac attgtcagaa    7980
gagtcgtcta ttttgaagtt ccctggtgtc cttattcgaa cttccacaga aagaccgaaa    8040
gtactagata aggtacggt tattgtaggt ggtattacct ataacaatct aatccaatcc     8100
gttgaactag caagagagat gcaaacaat acgaaccga tgattgatgc tattgattat       8160
aaagacacta acgtttcgac aaaggtagtt aaaattattc aaagctataa agatattatc    8220
aatcgaaata cttggaggaa atgacgatga ggatagcgat tgaaaagata attggtttgc    8280
tgaaaaacca gtcctctaaa gaatcgaatg ttaagattca tcgcttggcg tatattacaa    8340
actcaaaatt tgatggcaat aactatatag atagatggtg taaaatcagg aattctcaca    8400
ttggtgaata cagttatatt ggatttggta gtgattttaa taatgtagaa gtaggaagat    8460
```

```
attgttcgat atcttcggat gtaaaaattg ggttaggaaa acatcctaca cactttttta    8520
gctcatcacc gattttttat tctaataata atccatttaa cataaagcaa aagtttatag    8580
actttaatga ccaaccaagc cgtacaacaa ttaaaaatga tgtgtggatt ggtgcaaatg    8640
taattattat ggatggatta acaataaata ctggtgcagt catagcagcc ggctcagttg    8700
ttactaaaaa tgtaggagca tatgaggttg ttggtggggt tcctgcaaaa gtgattaaga    8760
agcgatttga caataaaaca attgaaaaac ttttggaaag caagtggtgg gagaaaacgc    8820
ctgacaaact aaaaggattt tcggttgaat atttaaataa aaaggatact taatgatatg    8880
agaattttaa atattgtatc gagtaatatt gttcaagacc caagggtact taaacaaata    8940
gaaacaatta aaggcgttac gaatgattat aaaattgttg aatgaataa ttcacaagct    9000
actaataggc gattggaaaa tttagattgt aattatcgtt tgttaggtag caaggtagat    9060
cccaaaaata ttctttctaa attaattaag cgtataagat ttgcaacagg tgttatccga    9120
gaaattaaag cttttaaacc tgacgtgatt catgcaaatg atttcgacgt attattaatg    9180
gtctatttaa gcaattataa aaaagctaat attgttatg atgcgcatga atatatgcg    9240
aaaaatgcct ttattaataa agttccactt atttcaaagt ttgtagaaag tatagaaaaa    9300
cacatagtaa aacatcgtgt taatgccttc gtaacagtaa gtcatgcagc aaaagaatat    9360
tatcaatcta aaggatataa gaaggaagcg aatgttatta cgaatgcacc tattttaaat    9420
gatagcagag aatttaaaga aatcgaaaac tttaaagaaa tcgtatatca aggtcaaatt    9480
gtaatggaca gaggatatga agagtttatt attgcttcat cagcttttaa acaaaatgct    9540
ccttcattca taattcgagg gtttggtccg catgaagaag tgataaaaga actgattagt    9600
tataactcgg aaaatattag gttggataaa ccagttgaag taaaagaatt ggttgataag    9660
ttagcagaaa gtaatgttgg tgttatcttg acgaaacctg tatctattaa ttttgaatat    9720
acagtatcta ataaaatttt tgaatgtata catgctggtt taccagtaat tttatctcct    9780
gtcaaagagc atatttatct caatgaaaaa tataaatttg gcattgtttt aaaggaagtt    9840
acgccgttag aaattgaaaa ggcggttaga aaattaagag ataatcacga tttgtttaat    9900
catttacgtc aaaatgcaat taaggcgtct aaaattttga attggcaaat agaaagtgaa    9960
cgattagtag aattatataa attttaaaga gaggtaaact atgaaatttt ttgtactttg    10020
tgcaattatc agcatgaaca tatttatagt aatctctaca tttactaaag aagtattagg    10080
gttccctata gagccggtgt attactcaac catggttggt atagcattaa ttactacggt    10140
gtttgctatt tataagataa ttgtcacgca agaaattccg cgagggttaa tattattaat    10200
tgctatatgt ttgcttttatc tagcttttta ttattttca ccagataagg aagagaaact    10260
agctaaaaat aatattctat tcttttttaac atgggcagtt ccagcggcaa ttagtggtat    10320
ttatattaaa tatataaaca aggctacggt agaaagattt tttaaattag tattttttcat    10380
attttctatt tcatttattt ttgtaatttt aataccaaaa cttacaggtg agatacctag    10440
ctatatcaat tttggactta tgaactatca aaacgcttcg tacctttcag catttactgc    10500
cggattaggc atttatttca ttatgaaagg ttcagtgaaa cataagtgga tatatgttct    10560
atttacaata attgatatcc ctattgtgtt tataccagga gggcgtggag gtgctatttt    10620
attaattctt tacggcttat ttgcatttat acttattacg tttaaaagag gaataccctat    10680
tgcagtaaaa agcattatgt atattttttgc attaagcata tctagtgtat tgatttactt    10740
tcttttttaca aaaggttcga atactagaac attttcatat ctacaaggtg gaacacttaa    10800
```

```
tttagaaggt acttctggaa gaggaccgat ttatgaaaaa ggtatttact ttattcaaca    10860
aagtccgtta ttaggctatg ggccatttaa ctattataaa ctaatcggaa atataccaca    10920
taacatcatt attgagttga ttctatcatt tggcttatta gggttttta tcataatgat     10980
ttgcattttg ctactagttt ataaaatgat taggaactat gatccaaaca ctatagattt    11040
actcgttatg tttatagcaa tctatccaat cacattatta atgtttagtt caaattattt    11100
agttgtaagt gaattttggt ttgtgttgtt ctattttatt acaaaaggac ggcgtcatca    11160
tggttaagaa agttttatt atggatagcg taaagacaat aattggtacg ttgcttatag     11220
ctttaggatt acaatttta gcttatccaa ttattaatca acgagtaggt aatgaagcgt     11280
ttggttctat tttaacgatt tatacaataa taacaatcac gagtgttgta ttaggcaata    11340
cgcttaacaa tatacgatta attaatatga atctatacaa atccaatcat tactactgga    11400
aatttgtgtc gatactttta atttcaattc tgattgagag tatagcttta attattgtat    11460
ttctttactt ttttaatttg aacaccatcg atattatctt tttaattcta cttaatattt    11520
taatgtgttt aaggatttat ctgaatgtat tttttaggat gactttaaaa tataatcaga    11580
ttttgtatat tgctcttatt caattttag gtttgctgat aggactattt ctatattatt     11640
taatccaaaa ctggattgtt tgttttatta ccagtgaatt gtttgcaacg atatatacat    11700
tggttaaatt acgggatta actataggcg agtatcaaag tgaagataat aatgtggtca     11760
aagattatgt gatgctactg agtacaaata gccttaataa tttgaatctc tacttagata    11820
gattaatctt attccaatt ataggtggaa cagctgtaac tatatcattt ctttcaacat     11880
ttattgggaa aatgttagct acatttctgt atccgattaa taatgtagta ctttcatata    11940
tttctgtaaa tgaaagcgac aatataaaga agcaatattt gaaaactaat ctatttgcta    12000
tagctgcact atgtttagtc atgattatat gttatccaat tacattaatt attgtctctt    12060
tactgtataa cattgattca agtttatatt cgaagtttat tatttaggt aatataggtg      12120
ttttattcaa tgcagtgagt attatgatcc aaactttaaa tacaaaacac gcatcaataa    12180
cattacaagc gaattatatg acgcttcaca cgattacatt tatattcata actattttaa    12240
tgacaattgc gtttggtcta aatggattct tttggacaac gctgttcagc aacattatta    12300
agtatgtgat tttaaatatt ataggtttaa agtctaaatt cattaataaa aaggacgtcg    12360
attagatgag tgaaaaaaag atttttgattt tatgtcagta tttttatccg gaatatgtat   12420
cttctgcgac gttaccaact caattggcgg aagatttaat tgcgaatcac attaatgtcg    12480
atgtcatgtg tggatggcca tatgaatata gtaatcataa acaggtttct aaaaccgaga    12540
tgcatcgtgg aattcgcatt cgacgtctca agtattcgag gtttaataac aaaagtaagg    12600
ttggaaggat catcaatttc tttagtttat tttcaaaatt cgtgattaat atacctaaaa    12660
tgttgaaata tgatcagatt cttgtttact ctaatccacc aatcttgcca ttaataccag    12720
acgttttaca cagactgctt aagaaaaaat attcttttgt ggtgtatgat atagcacctg    12780
ataatgcgat taagacaggt gcaactcgtc caggtagcat gattgataag ctgatgcgtt    12840
acattaatag acatgtctac aagaatgctg aaaatgtcat tgtccttggt acggaaatga    12900
aaaactactt actaaatcat caaatttcta aaaatgctga caatatccat gtgattccta    12960
actggtatga catgcgtcaa ttacaagaca atcgtatcta taatgacaca tttaaagctt    13020
accgtgagca atacgacaaa attttattgt atagcggtaa tatggggcag ttacaggata    13080
tggagacact tatctcattt ttaaaattaa ataaggatca gcctcaaacg ttaacaatac    13140
tttgtggtca tggtaagaaa tttgcagatg tcaaaacggc aatagaagac catcgtattg    13200
```

```
aaaatgttaa aatgtttgag tttttaacag gtacagacta tgctgacgta ttaaaaattg   13260
cggatgtatg tattgcatcg ctgattaaag aaggcgtcgg tttaggcgtt ccgagcaaga   13320
attatggcta ccttgcagct aagaaaccgt tggtactcat catggataag caatctgata   13380
tcgttcaaca tgttgaacaa tatgatgcgg gtatccaaat tgataatggc gatgcacatg   13440
ccatttataa cttcatcaac actcactcga gtaaggaatt gcacgagatg ggtgagcgcg   13500
cacatcaact gtttaaagat aaatatacga gagaaattaa tactatgaag tattacaatc   13560
tgttgaagtg aggagataat tatgaagcga ttattcgatg tagtgagttc aatatatggt   13620
ttagtagttt taagtccgat tctgttaatt acagcattac taattaaaat ggaatcacct   13680
ggaccagcca ttttcaaaca aaaaagaccg acgattaata atgaattgtt taatatttat   13740
aagtttagat caatgaaaat agacacacct aatgttgcaa ctgatttaat ggattcaaca   13800
tcgtatataa caaagacagg gaaggtcatt cgtaagacct ctattgatga attgccacaa   13860
ttattgaatg ttttaaaagg agaaatgtca attgtaggtc ctagaccagc gctttataat   13920
caatacgaat taatcgaaaa acgtacaaaa gcgaacgtgc atacgattag accaggtgtg   13980
acaggactag ctcaagtgat ggggagagat gatattactg atgatcaaaa agtagcgtat   14040
gatcattatt acttaacaca tcaatctatg atgcttgata tgtatatcat atataaaaca   14100
attaaaaata tcgttacttc agaaggtgtg catcactaat gagaaaaaat atttttaatta  14160 caggcgtaca tggatatatc ggtaatgctt aaaagataa gcttattgaa caaggacatc    14220
aagtagatca aattaatgtt aggaatcaat tatggaagtc gacctcgttc aaagattatg   14280
atgttttaat tcatacagca gctttggttc acaacaattc acctcaagca aggctatctg   14340
attatatgca agtgaatatg ttgcttacga aacaattggc acaaaaggct aaagctgaag   14400
acgttaaaca atttatttt atgagtacta tggcagttta tggaaaagaa ggtcaggttg    14460
gtaaatcaga tcaaattgat acacaaacac caatgaaccc tacgaccaac tatggtattt   14520
ccaaaaagtt cgctgaacaa gcattacaag agttgattag tgattcgttt aaagtagcaa   14580
ttgtgagacc accaatgatt tatggtgcac attgcccagg aaatttccaa cggttaatgc   14640
aattgtcaaa gcgactgcca atcattccca atattaacaa tcagcgcagt gcattatata   14700
ttaaacatct gacagcattt attgatcaat taatatcatt agaagtgaca ggcgtgtatc   14760
atcctcaaga tagtttttac tttgatacat cgtcagtaat gtatgaaata cgtcgccaat   14820
cacatcgtaa aacggtattg atcaacatgc cttcagtgtt aaataagtat tttaataagt   14880
tgtcggtctt tagaaaatta ttcggcaatt taacatacag caatacgtta tatgaaaata   14940
ataatgcact tgaagttatt cctggaaaaa tgtcacttgt tattgcggac atcatggatg   15000
aaacgacaac caaagataag gcataagtca tctattaaat aaaatcaaca tacaaatcgt   15060
tttatttgga ggttatagta tgaagttaac agtagttggc ttaggttata ttggtttacc   15120
aacatcaatt atgtttgcaa agcatggcgt cgatgtgctt ggtgttgata ttaatcagca   15180
aacgattgat aagttacaaa gtggtcaaat tagtattgaa gaacctgggt tacaagaggt   15240
ttatgaagag gtactgtcat cgggaaaatt gaaggtatct acaacgccag aagcatctga   15300
tgtttttatc attgccgttc cgacgccgaa taatgatgat cagtaccggt catgtgacat   15360
ttcgctagtt atgcgtgcat tagatagtat tttaccattt ttagaaaaag gaatactat    15420 tattgtagag tcgacaattg cgcctaaaac gatggatgat tttgtaaaac cagtcattga   15480
aaatttagga tttacaatag gtgaagatat ttgtttagtg cattgtccag aacgtgtact   15540
```

-continued

```
gccaggaaaa attttagaag aattagttca taacaatcgt atcattggcg gtgtgactaa    15600
agcttgtatt gaagcgggta aatatgtcta tcgcacattc gttcagggag aaatgattga    15660
aacagatgca cgtactgctg aaatgagtaa gctaatggaa aacacatata gagacgtgaa    15720
tattgcttta gctaatgaat taacaaaaat ttgcaataac ttaaatatta atgtattaga    15780
tgtgattgaa atggcaaaca acatccgcg tgttaatatc catcaacctg gtccaggtgt    15840
aggcggtcat tgtttagctg ttgatccgta ctttattatt gctaaagacc ctgaaaatgc    15900
aaagttaatt caaactggac gtgaaattaa taattcaatg ccggcctatg ttgttgatac    15960
aacgaagcaa atcatcaaag cgttgagcgg gaataaagtc acagtatttg gtttaactta    16020
taaaggtgat gttgatgata aagagaatc gccagcattt gatatttatg agctattaaa    16080
tcaagaacca gacatagaag tatgtgctta tgatccacat gttgaattag attttgtgga    16140
acatgatatg tcacatgctg tcaaagacgc atcgctagta ttgatttaa gtgaccactc    16200 agaatttaaa aatttatcgg acagtcattt tgataaaatg aagcataaag tgattttga    16260 tacaaaaaat gttgtgaaat catcatttga agatgtatcg tattataatt atggcaatat    16320
atttaatttt atcgacaaat aaaatgtgtc aaactagggc atacatgatt aaggaaagat    16380
aagctgtcat gtgtttgaac ttcagagagg ataatgttat gaaaaaaatt atggttattt    16440
tcggtacgag acccgaagca ataaaaatgg caccattagt aaaagaaatt gatcataatg    16500
ggaactttga agcgaacatt gtgattacag cacaacatag agatatgtta gatagtgtgt    16560
taagtatatt tgatattcaa gctgatcatg atttaaatat tatgcaagat caacaaacgt    16620
tagcggacct tacggcgaat gcgcttgcta aacttgatag catcattaat gaggaacagc    16680
cggatatgat tttagtacat ggtgatacta caacgacttt tgtaggaagt ttggcagcat    16740
tttatcatca aattccggtt ggacatgtag aagctggact tcgaacacat cagaaatact    16800
caccatttcc tgaagagtta aatcgagtca tggtaagtaa tattgctgaa ttgaattttg    16860
cgccaacagt aattgcagct aaaaatttac tttttgaaaa caaagacaaa gagcgtatct    16920
ttattactgg aaatacagtt attgacgcat tgtcaacaac agttcaaaat gattttgttt    16980
caacgattat taataaacat aaaggcaaga agttattttt actaacagcg catcgtcgtg    17040
aaaatattgg ggaaccgatg catcagattt ttaaagcagt aagagatttg gcagatgaat    17100
ataaagatgt tgtcttcatt tatccaatgc atcgtaatcc aaaggtaaga gcgattgccg    17160
aaaaatattt atctgggaga aatcggattg aattaattga gccattagat gcgattgagt    17220
tccataattt tacaaatcaa tcgtacctcg tgctgacaga ttctggtggt attcaagagg    17280
aggctcctac atttggaaaa cctgtgttgg tattaaggaa tcatacagag cgtcccgaag    17340
gcgttgaggc gggaacatcg agagtaattg gcacagatta tgacaatatt gttcgaaatg    17400
tgaaacaatt gattgaggat gatgaagcgt atcaacgtat gagtcaagcg aataatccat    17460
atggtgatgg acaagcatca cgacgtattt gtgaagcaat agaatattat tttggattgc    17520
gctcagacaa gccggatgaa ttcgtaccttt acgtcacaa ataata    17566
```

<210> SEQ ID NO 7
<211> LENGTH: 16342
<212> TYPE: DNA
<213> ORGANISM: Staphylococcus aureus

<400> SEQUENCE: 7

```
gagtctacaa gcgattaaat tgacgttcga atatttaaaa tcatctgttg aaaagggtga      60
taaagtttca agagagaaaa tgcataacgc atcaactttg gctggtatgg catttgcaaa     120
```

```
tgcattctta ggcattgcac actcaattgc acataaaatt ggtggcgaat atggtattcc    180
gcatggtaga gcgaatgcga tattactacc gcatattatc cgttataatg ccaaagaccc    240
gcaaaaacat gcattattcc ctaaatatga gttcttcaga gcagatacag attatgcaga    300
tattgccaaa ttcttaggat aaaagggaa tacgacagaa gcactcgtag aatcattagc     360
taaagctgtc tacgaattag gtcaatcagt cggaattgaa atgaatttga atcacaagg    420 tgtgtctgaa gaagaattaa atgaatcaat tgatagaatg gcagagctcg catttgaaga    480
tcaatgtaca actgctaatc ctaaagaagc actaatcagt gaaatcaaag atatcattca    540
aacatcatat gattataagc aataatctat ctgataataa tcatataact cacctgaaat    600
tacaaaagta aaaatgcca cataaacttt aagtcgataa tcattttacg gttatcggct     660
tttatttatt gccaaatctt cagagataca aactagacaa tcattttttt aaataaagaa    720
aatattaaga ttgatactca tttcgcaaac tattactact ttagagccat ggccacagta    780
taaattatat cagtatgctt ataattttt tgaaatcttt aaacaaatga agtaataatt     840
gagaaaagtg tagttaaatt attttcttg aaattatttg ttacatagca tttcgatgta     900
aaattcactt tttataagta aatttaaaaa gagtttgcaa aatatacagg ggattatata    960
taatggaaaa caagaaagga aaataggagg tttatatgga aagtacatta gaattaacaa    1020
aaattaaaga agtattacaa aaaaacttga agattttaat tattttaccg ctattatttt    1080
taattattag cgctattgtt acattttcg tcttatcacc taaatatcaa gctaatactc     1140
aaatcttagt gaatcaaact aagggtgaca atcctcagtt tatggcacaa gaggttcaaa    1200
gtaatattca acttgtaaat acgtataaag aaattgttaa agtcctaga atttagatg      1260 aggtgtcaaa ggacttaaat gataagtatt caccatctaa atttgtcgag tatgttgacaa    1320 ttacaaacca agaaaatacg caacttatca acatccaagt taaaagtggt cataaacaag    1380
attcggaaaa aattgcgaat agcttcgcta agttacaag taaacaaatt ccgaagatta     1440
tgagtgtgga taacgtatca atttatctca agcagacgg tacagcagtt aaagtcgcac    1500 caaaactgt agtgaatcta atcggtgcat tctttttagg attagttgtc gcgcttatat    1560
atatcttctt caaagtaatt ttcgataagc gaattaaaga tgaagaagat gtagagaaag    1620
aattaggatt gcctgtattg ggttcaattc aaaaatttaa ttaaggatgg ttgctactta    1680
tgtcaaaaaa ggaaaatacg acaacaacac tatttgtata tgaaaaacca aaatcaacaa    1740
ttagtgaaaa gtttcgaggt atacgttcaa acatcatgtt ttcaaaagca aatggtgaag    1800
taaagcgctt attggttact tctgaaaagc ctggtgcagg taaaagtaca gttgtatcga    1860
atgtagcgat tacttatgca caagcaggct ataagacatt agttattgat ggcgatatgc    1920
gtaagccaac acaaaactat attttaatg agcaaaataa taatggacta tcaagcttaa    1980
tcattggtcg aacgactatg tcagaagcaa ttacgtcgac agaaattgaa atttagatt     2040 tgctaacagc tggccctgta cctccaaatc catctgagtt aattgggtct gaaaggttca    2100
aagaattagt tgatctgttt aataaacgtt acgacattat tattgtcgat acaccgccag    2160
ttaatactgt gactgatgca caactatatg cgcgtgctat taagatagt ctgttagtaa     2220 ttgatagtga aaaaaatgat aaaaatgaag ttaaaaaagc aaaagcactt atggaaaaag    2280
caggcagtaa cattctaggt gtcatttga acaagacaaa ggtcgataaa tcttctagtt     2340
attatcacta ttatggagat gaataagtat gattgatatt cataaccata tattgcctaa    2400
tatcgatgac ggtccgacaa atgaaacaga gatgatggat cttttaaaac aagcgacaac    2460
```

```
acaaggtgtt acagaaatca ttgtaacatc acatcactta catcctcgat ataccacacc    2520
tatagaaaaa gtgaaatcat gtttaaacca tattgaaagc ttagaggaag tacaagcact    2580
aaatctaaag ttttattatg gtcaggaaat aagaattacc gatcaaatcc ttaatgatat    2640
tgatcgaaaa gttattaccg gtattaatga ttcacgctat ttactaatag aatttccatc    2700
aaatgaagtt ccacactata ctgatcaatt attttttcgaa ttacagagta aaggctttgt    2760
accgattatt gcacatccag agcgaaataa agcaataagt caaaaccttg acatactata    2820
cgatttaatt aacaaggtg ctttaagtca agtgacaacg gcgtcattag cgggtatttc    2880
cggtaaaaaa attagaaaat tagcaattca aatgattgaa aacaatctga cacatttcat    2940
cggttcagat gcgcataaca cagaaatcag accgttctta atgaaagact tatttaatga    3000
taagaaatta cgtgattatt atgaagatat gaacggattt attagtaatg cgaagttagt    3060
tgttgatgat aaaaaaattc ctaaacgaat gccacaacaa gattataaac agaaaagatg    3120
gtttgggtta taaacagcaa atgaggggtt ttatggcaca tttatctgtg aaattgcggc    3180
ttttaatact agcattaatc gattcactga tagtgacatt ttcagtattc gtaagttatt    3240
acattttaga accgtatttc aaaacatatt ctgtcaaatt attaatattg gcagctatat    3300
cactattcat atcgcatcat atttcagcat ttatttttaa tatgtatcat cgagcgtggg    3360
aatatgccag tgtgagtgaa ttgattttaa ttgttaaagc tgtgacgaca tctatcgtta    3420
ttacgatggt ggtcgtgaca attgttacag gcaatagacc gttttttaga ttgtatttaa    3480
ttacttggat gatgcacttg attttaatag gtggctcaag gttatttttgg cgtatttatc    3540 ggaaatacct tggaggtaag tcatttaata agaagccaac tttagttgtt ggtgctggtc    3600
aagcaggttc aatgctgatt agacaaatgt tgaaaagtga cgaaatgaaa cttgaaccgg    3660
tattagcagt cgatgatgac gaacataaac gcaatatcac aattactgag ggtgtaaaag    3720
tccaaggtaa aattgcggat attccagaac tagtgaggaa atataagatt aaaaaaatca    3780
tcattgcaat tccaactatt ggtcaagagc gtttgaaaga aattaataat atttgccata    3840
tggatggcgt tgagttattg aaaatgccaa atatagaaga cgtcatgtct ggtgagttag    3900
aagtgaatca actgaaaaaa gttgaagtag aagatttact aggcagagat cctgttgaat    3960
tagatatgga tatgatatca aatgaattga cgaataaaac tattttagtt acgggtgcag    4020
gtggttcaat aggatcagaa atttgtagac aagtttgtaa tttctatcca gaacgtatta    4080
ttctacttgg ccatggtgaa aacagtattt atttaatcaa tcgtgaattg cgaaatcgct    4140
tcggaaaaaa tgttgatatc gttcctatta tagcggatgt gcaaaataga gcgcgtatgt    4200
ttgaaattat ggaaacgtat aaaccatacg cagtttatca tgcagcagca cacaagcacg    4260
tgccgttaat ggaagacaac cctgaagaag cagtacataa taatattta ggtacgaaaa    4320 atactgctga agctgctaaa aatgcagagg taaagaaatt cgttatgatt tctacggata    4380
aagccgttaa tccgcctaat gtcatgggag cttcaaagcg aattgcagaa atgattattc    4440
aaagtttaaa tgatgaaacg catcgaacaa attttgttgc agtgagattt ggtaatgtac    4500
ttggatcgag aggatctgtg attccacttt tcaaaagtca aattgaagaa ggtgggccag    4560
ttactgtgac acatcctgaa atgacacgtt acttatgac aattcctgaa gcttctagac    4620
tagttttgca ggcaggggca ttagcagaag gtggcgaagt atttgtgcta gatatggag    4680 aaccagtgaa aattgtagat ttggcacgta atttaattaa gctaagtggt aaaaaagaag    4740
acgacatacg cattacttat acagggatta gaccccggcga aaaatgtttt gaagagctta    4800
tgaataaaga tgaggttcat cctgaacaag tatttgaaaa aatttatcgt ggcaaagtac    4860
```

```
aacatatgaa atgtaatgaa gttgaagcga ttattcaaga catcgtcaat gactttagta    4920
aagaaaaaat tattaactat gccaatggca aaaagggaga taattatgtt cgatgacaaa    4980
attttattaa ttactggggg cacaggatca ttcggtaatg ctgttatgaa acggttttta    5040
gattctaata ttaaagaaat tcgtattttt tcacgcgatg agaaaaaaca agatgacatt    5100
cgaaaaaaat ataataattc aaaattaaag ttctacattg gtgatgtgcg tgatagtcaa    5160
agtgtagaaa cagcaatgcg agatgttgat tacgtattcc atgcagcagc tttaaaacaa    5220
gtgccgtcat gtgaattctt ccagttgag gcagtgaaga caaatattat tggtacagaa     5280
aatgtcttac aaagtgctat tcatcaaaat gttaaaaaag tcatatgttt atctacagat    5340
aaggcagcgt atcctattaa tgctatgggt atttcaaaag caatgatgga aaaagtattc    5400
gtagccaaat caagaaatat tcgtagtgaa caaacgctta tttgtggtac aagatacggt    5460
aatgtgatgg cttcaagagg atcagtaata cctttgttta tcgacaaaat caaagctgga    5520
gaacctttaa cgattacaga tcctgatatg acaagatttt taatgagctt agaagatgcg    5580
gtagaactag ttgttcatgc atttaagcat gcagagacag gagatattat ggttcaaaaa    5640
gcaccaagct caacggtagg ggatcttgcg accgcattat tagaattgtt tgaagctgat    5700
aatgcaattg aaatcattgg tacgcgacat ggagagaaaa aagcagaaac attgttgacg    5760
agagaagaat acgcacaatg tgaagatatg ggtgattatt ttagagtgcc ggcagactcc    5820
agagatttaa attatagtaa ttatgttgaa accggtaacg aaaagattac gcaatcttat    5880
gaatataact ccgataatac acatatttta acggtggaag agataaaaga aaaacttttta   5940
acactagaat atgttagaaa cgaattgaat gattataaag cttcaatgag ataggagaga    6000
ttgacgttga atattgtaat tacagagca aaaggttttg taggaaaaaaa cttgaaagca    6060
gatttaacat caacgacaga tcatcatatt ttcgaagtac atcgacaaac taaagaggaa    6120
gaattagagt cagcattgtt gaaagcagac tttatcgtgc atttagcggg tgttaatcga    6180
cctgaacatg acaaagaatt cagcttagga aacgtgagtt atttagatca tgtacttgat    6240
atattaacta gaaatacgaa aaagccagcg atattattat cgtcttcaat acaagcaaca    6300
caagataatc cttatggtga gagtaagttg caaggggaac agctattaag agagtatgcc    6360
gaagagtatg gcaatacggt ttatatttat cgctggccaa atttattcgg caagtggtgt    6420
aagccgaatt ataactcagt gatagcaaca ttttgttaca aaattgcacg taacgaagag    6480
attcaagtta atgatcggaa tgttgaacta acgctaaact acgtggatga tatcgtcgct    6540
gaaataaagc gtgctattga aggaactcca acgattgaaa atggtgtacc tacagtacca    6600
aacgtattta aagtgacatt gggagaaatt gtagatttat tatacaagtt caaacagtca    6660
cgtctcgatc gaacattgcc gaaattagat aacttgtttg aaaaagattt gtatagtacg    6720
tatttaagct atctacctag tacagacttt agttatccct tacttatgaa tgtggatgat    6780
aggggttctt ttacagaatt tataaaaaca ccggatcgtg gtcaagtttc tgtaaatatt    6840
tctaaaccag gtattactaa aggtaatcac tggcaccata ctaaaaacga aaaatttcta    6900
gtcgtatcag gtaaagggt aattcgtttt agacatgtta atgatgatga atcattgaa     6960
tattacgttt ctggcgataa attagaagtt gtagacatac cagtaggata cacacataat    7020
attgaaaatt taggcgacac agatatggta actattatgt gggtgaatga aatgtttgat    7080
ccaaatcagc cagatacgta tttcttggag gtatagcgca tggaaaaact gaaattaatg    7140
acaatagttg gtacaaggcc tgaaatcatt cgtttatcat caacgattaa agcatgtgat    7200
```

-continued

```
caatatttta atcagatatt agtacacact ggtcaaaatt atgattatac attgaatcaa    7260
attttctttg atgatttgga attaagacaa ccggaccact acttagaggc agttggaagt    7320
aaccttggag aaacgatggg gaatattatt gcgaagacat atgacgtttt attacgcgaa    7380
caaccagatg cacttttaat tcttggtgat acaaatagtt gtttagcagc agtatctgct    7440
aaacgattaa agattcctgt gttccacatg gaagcgggta atagatgctt tgatcagaat    7500
gtacctgaag aaatcaatcg taaaattgtt gaccatgtca gtgatgtgaa tctaccttat    7560
acagaacata gcagacggta tttattagat gaaggcttca ataaagcgaa tatctttgtg    7620
acaggatcac cgatgacaga agtgatagaa gcgcatcgag ataaaattaa tcacagtgac    7680
gttttaaata aactaggatt agaaccgcaa caatacattt agtatctgc gcatagagaa     7740 gagaatatcg ataatgaaaa gaattttaaa tcattaatga atgcgataaa tgatattgcc    7800
aaaaagtata aaatgcctgt gatttattca acgcatccaa gaagttggaa gaaaattgaa    7860
gaaagtaaat ttgaatttga tccattagtt aaacagttaa agccatttgg tttctttgat    7920
tataatgcat tgcaaaaaga tgcatttgtt gtgctatcag atagtggaac attgtcagaa    7980
gagtcgtcta ttttgaagtt ccctggtgtc cttattcgaa cttccacaga aagaccggaa    8040
gtactagata aaggtacggt tattgtaggt ggtattacct ataacaatct aatccaatcc    8100
gttgaactag caagagagat gcaaaacaat aacgaaccga tgattgatgc tattgattat    8160
aaagacacta acgtttcgac aaaggtagtt aaaattattc aaagctataa agatattatc    8220
aatcgaaata cttggaggaa atgacgatga ggatagcgat tgaaaagata attggtttgc    8280
tgaaaaacca gtcctctaaa gaatcgaatg ttaagattca tcgcttggcg tatattacaa    8340
actcaaaatt tgatggcaat aactatatag atagatggtg taaaatcagg aattctcaca    8400
ttggtgaata cagttatatt ggatttggta gtgattttaa taatgtagaa gtaggaagat    8460
attgttcgat atcttcggat gtaaaaattg ggttaggaaa acatcctaca cactttttta    8520
gctcatcacc gatttttat tctaataata atccatttaa cataaagcaa aagtttatag     8580
actttaatga ccaaccaagc cgtacaacaa ttaaaaatga tgtgtggatt ggtgcaaatg    8640
taattattat ggatggatta acaataaata ctggtgcagt catagcagcc ggctcagttg    8700
ttactaaaaa tgtaggagca tatgaggttg ttggtggggt tcctgcaaaa gtgattaaga    8760
agcgatttga caataaaaca attgaaaaac ttttggaaag caagtggtgg gagaaaacgc    8820
ctgacaaact aaaaggattt tcggttgaat atttaaataa aaaggatact taatgatatg    8880
agaattttaa atattgtatc gagtaatatt gttcaagacc caagggtact taaacaaata    8940
gaaacaatta aaggcgttac gaatgattat aaaattgttg gaatgaataa ttcacaagct    9000
actaataggc gattggaaaa tttagattgt aattatcgtt tgttaggtag caaggtagat    9060
cccaaaaata ttcttttctaa attaattaag cgtataagat ttgcaacagg tgttatccga    9120
gaaattaaag cttttaaacc tgacgtgatt catgcaaatg atttcgacgt attattaatg    9180
gtctatttaa gcaattataa aaaagctaat attgtttatg atgcgcatga atatatgcg     9240 aaaaatgcct ttattaataa agttccactt atttcaaagt ttgtagaaag tatagaaaaa    9300
cacatagtaa aacatcgtgt taatgccttc gtaacagtaa gtcatgcagc aaaagaatat    9360
tatcaatcta aaggatataa gaaggaagcg aatgttatta cgaatgcacc tattttaaat    9420
gatagcagag aatttaaaga aatcgaaaac tttaagaaaa tcgtatatca aggtcaaatt    9480
gtaatggaca gaggatatga agagtttatt attgcttcat cagctttaa acaaaatgct     9540 ccttcattca taattcgagg gtttggtccg catgaagaag tgataaaaga actgattagt    9600
```

```
tataactcgg aaaatattag gttggataaa ccagttgaag taaaagaatt ggttgataag   9660
ttagcagaaa gtaatgttgg tgttatcttg acgaaacctg tatctattaa ttttgaatat   9720
acagtatcta ataaaatttt tgaatgtata catgctggtt taccagtaat tttatctcct   9780
gtcaaagagc atatttatct caatgaaaaa tataaatttg gcattgtttt aaaggaagtt   9840
acgccgttag aaattgaaaa ggcggttaga aaattaagag ataatcacga tttgtttaat   9900
catttacgtc aaaatgcaat taaggcgtct aaaattttga attggcaaat agaaagtgaa   9960
cgattagtag aattatataa attttaaaga gaggtaaact atgaaatttt ttgtactttg  10020
tgcaattatc agcatgaaca tatttatagt aatctctaca tttactaaag aagtattagg  10080
gttccctata gagccggtgt attactcaac catggttggt atagcattaa ttactacggt  10140
gtttgctatt tataagataa ttgtcacgca agaaattccg cgagggttaa tattattaat  10200
tgctatatgt ttgctttatc tagcttttta ttattttca ccagataagg aagagaaact  10260
agctaaaaat aatattctat tcttttaac atgggcagtt ccagcggcaa ttagtggtat  10320
ttatattaaa tatataaaca aggctacggt agaaagattt tttaaattag tattttttcat  10380 attttctatt tcatttattt ttgtaatttt aataccaaaa cttacaggtg agatacctag  10440
ctatatcaat tttggactta tgaactatca aaacgcttcg tacctttcag catttactgc  10500
cggattaggc atttatttca ttatgaaagg ttcagtgaaa cataagtgga tatatgttct  10560
atttacaata attgatatcc ctattgtgtt tataccagga gggcgtggag gtgctatttt  10620
attaattctt tacggcttat ttgcatttat acttattacg tttaaaagag gaataccat  10680 tgcagtaaaa agcattatgt atattttgc attaagcata tctagtgtat tgatttactt  10740 tcttttaca aaaggttcga atactagaac attttcatat ctacaaggtg gaacacttaa  10800
tttagaaggt acttctggaa gaggaccgat ttatgaaaaa ggtatttact ttattcaaca  10860
aagtccgtta ttaggctatg gccatttaa ctattataaa ctaatcggaa ataccaca  10920 taacatcatt attgagttga ttctatcatt tggcttatta gggttttta tcataatgat  10980 ttgcatttg ctactagttt ataaaatgat taggaactat gatccaaaca ctatagtttt  11040
actcgttatg tttatagcaa tctatccaat cacattatta atgtttagtt caaattattt  11100
agttgtaagt gaattttggt ttgtgttgtt ctatttatt acaaaaggac ggcgtcatca  11160
tggttaagaa agttttttatt atggatagcg taaagacaat aattggtacg ttgcttatag  11220
ctttaggatt acaatttta gcttatccaa ttattaatca acgagtaggt aatgaagcgt  11280
ttggttctat tttaacgatt tatacaataa taacaatcac gagtgttgta ttaggcaata  11340
cgcttaacaa tatacgatta attaatatga atctatacaa atccaatcat tactactgga  11400
aatttgtgtc gatacttta atttcaattc tgattgagag tatagcttta attattgtat  11460
ttctttactt ttttaatttg aacaccatcg atattatctt tttaattcta cttaatatttt  11520 taatgtgttt aaggattat ctgaatgtat tttttaggat gactttaaaa tataatcaga  11580
ttttgtatat tgctcttatt caatttttag gtttgctgat aggactattt ctatattatt  11640
taatccaaaa ctggattgtt tgttttatta ccagtgaatt gtttgcaacg atatatacat  11700
tggttaaatt acggggatta actataggcg agtatcaaag tgaagataat aatgtggtca  11760
aagattatgt gatgctactg agtacaaata gccttaataa tttgaatctc tacttagata  11820
gattaatctt attccaatt ataggtggaa cagctgtaac tatatcattt ctttcaacat  11880
ttattgggaa aatgttagct acatttctgt atccgattaa taatgtagta ctttcatata  11940
```

```
tttctgtaaa tgaaagcgac aatataaaga agcaatattt gaaaactaat ctatttgcta   12000
tagctgcact atgtttagtc atgattatat gttatccaat tacattaatt attgtctctt   12060
tactgtataa cattgattca agtttatatt cgaagtttat tattttaggt aatataggtg   12120
ttttattcaa tgcagtgagt attatgatcc aaactttaaa tacaaaacac gcatcaataa   12180
cattacaagc gaattatatg acgcttcaca cgattacatt tatattcata actatttaa    12240 tgacaattgc gtttggtcta aatggattct tttggacaac gctgttcagc aacattatta   12300
agtatgtgat tttaaatatt ataggtttaa agtctaaatt cattaataaa aaggacgtcg   12360
attagatgag tgaaaaaaag attttgattt tatgtcagta tttttatccg gaatatgtat   12420
cttctgcgac gttaccaact caattggcgg aagatttaat tgcgaatcac attaatgtcg   12480
atgtcatgtg tggatggcca tatgaatata gtaatcataa acaggtttct aaaaccgaga   12540
tgcatcgtgg aattcgcatt cgacgtctca agtattcgag gtttaataac aaaagtaagg   12600
ttggaaggat catcaatttc tttagtttat tttcaaaatt cgtgattaat atacctaaaa   12660
tgttgaaata tgatcagatt cttgtttact ctaatccacc aatcttgcca ttaataccag   12720
acgttttaca cagactgctt aagaaaaaat attcttttgt ggtgtatgat atagcacctg   12780
ataatgcgat taagacaggt gcaactcgtc caggtagcat gattgataag ctgatgcgtt   12840
acattaatag acatgtctac aagaatgctg aaaatgtcat tgtccttggt acggaaatga   12900
aaaactactt actaaatcat caaatttcta aaaatgctga caatatccat gtgattccta   12960
actggtatga catgcgtcaa ttacaagaca atcgtatcta taatgacaca tttaaagctt   13020
accgtgagca atacgacaaa atttttattgt atagcggtaa tatggggcag ttacaggata   13080
tggagacact tatctcattt ttaaaattaa ataaggatca gcctcaaacg ttaacaatac   13140
tttgtggtca tggtaagaaa tttgcagatg tcaaaacggc aatagaagac catcgtattg   13200
aaaatgttaa aatgtttgag ttttaacag gtacagacta tgctgacgta ttaaaaattg   13260
cggatgtatg tattgcatcg ctgattaaag aaggcgtcgg tttaggcgtt ccgagcaaga   13320
attatggcta ccttgcagct aagaaaccgt tggtactcat catggataag caatctgata   13380
tcgttcaaca tgttgaacaa tatgatgcgg gtatccaaat tgataatggc gatgcacatg   13440
ccatttataa cttcatcaac actcactcga gtaaggaatt gcacgagatg ggtgagcgcg   13500
cacatcaact gtttaaagat aaatatacga gagaaattaa tactatgaag tattacaatc   13560
tgttgaagtg aggagataat tatgaagcga ttattcgatg tagtgagttc aatatatggt   13620
ttagtagttt taagtccgat tctgttaatt acagcattac taattaaaat ggaatcacct   13680
ggaccagcca ttttcaaaca aaaaagaccg acgattaata atgaattgtt taatattat    13740 aagtttagat caatgaaaat agacacacct aatgttgcaa ctgatttaat ggattcaaca   13800
tcgtatataa caaagacagg gaaggtcatt cgtaagacct ctattgatga attgccacaa   13860
ttattgaatg ttttaaaagg agaaatgtca attgtaggtc ctagaccagc gctttataat   13920
caatacgaat taatcgaaaa acgtacaaaa gcgaacgtgc atacgattag accaggtgtg   13980
acaggactag ctcaagtgat ggggagagat gatattactg atgatcaaaa agtagcgtat   14040
gatcattatt acttaacaca tcaatctatg atgcttgata tgtatatcat atataaaaca   14100
attaaaaata tcgttacttc agaaggtgtg catcactaat gagaaaaaat attttaatta   14160
caggcgtaca tggatatatc ggtaatgctt taaagataa gcttattgaa caaggacatc    14220
aagtagatca aattaatgtt aggaatcaat tatggaagtc gacctcgttc aaagattatg   14280
atgttttaat tcatacagca gctttggttc acaacaattc acctcaagca aggctatctg   14340
```

```
attatatgca agtgaatatg ttgcttacga acaattggc acaaaaggct aaagctgaag    14400
acgttaaaca atttatttt atgagtacta tggcagttta tggaaaagaa ggtcaggttg    14460
gtaaatcaga tcaaattgat acacaaacac caatgaaccc tacgaccaac tatggtattt    14520
ccaaaaagtt cgctgaacaa gcattacaag agttgattag tgattcgttt aaagtagcaa    14580
ttgtgagacc accaatgatt tatggtgcac attgcccagg aaatttccaa cggttaatgc    14640
aattgtcaaa gcgactgcca atcattccca atattaacaa tcagcgcagt gcattatata    14700
ttaaacatct gacagcattt attgatcaat taatatcatt agaagtgaca ggcgtgtatc    14760
atcctcaaga tagtttttac tttgatacat cgtcagtaat gtatgaaata cgtcgccaat    14820
cacatcgtaa aacggtattg atcaacatgc cttcagtgtt aaataagtat tttaataagt    14880
tgtcggtctt tagaaaatta ttcggcaatt taacatacag caatacgtta tatgaaaata    14940
ataatgcact tgaagttatt cctggaaaaa tgtcacttgt tattgcggac atcatggatg    15000
aaacgacaac caaagataag gcataagtca tctattaaat aaaatcaaca tacaaatcgt    15060
tttatttgga ggtttatagta tgaagttaac agtagttggc ttaggttata ttggtttacc    15120
aacatcaatt atgtttgcaa agcatggcgt cgatgtgctt ggtgttgata ttaatcagca    15180
aacgattgat aagttacaaa gtggtcaaat tagtattgaa gaacctgggt tacaagaggt    15240
ttatgaagag gtactgtcat cgggaaaatt gaaggtatct acaacgccag aagcatctga    15300 tgttttatc attgccgttc cgacgccgaa taatgatgat cagtaccggt catgtgacat    15360
ttcgctagtt atgcgtgcat tagatagtat tttaccattt ttagaaaaag ggaatactat    15420
tattgtagag tcgacaattg cgcctaaaac gatggatgat tttgtaaaac cagtcattga    15480
aaatttagga tttacaatag gtgaagatat ttgtttagtg cattgtccag aacgtgtact    15540
gccaggaaaa attttagaag aattagttca taacaatcgt atcattggcg gtgtgactaa    15600
agcttgtatt gaagcgggta aatatgtcta tcgcacattc gttcagggag aaatgattga    15660
aacagatgca cgtactgctg aaatgagtaa gctaatggaa aacacatata gagacgtgaa    15720
tattgcttta gctaatgaat taacaaaaat ttgcaataac ttaaatatta atgtattaga    15780
tgtgattgaa atggcaaaca acatccgcg tgttaatatc catcaacctg gtccaggtgt    15840
aggcggtcat tgtttagctg ttgatccgta ctttattatt gctaaagacc ctgaaaatgc    15900
aaagttaatt caaactggac gtgaaattaa taattcaatg ccggcctatg ttgttgatac    15960
aacgaagcaa atcatcaaag cgttgagcgg gaataaagtc acagtatttg gtttaactta    16020
taaaggtgat gttgatgata aagagaatc gccagcattt gatatttatg agctattaaa    16080
tcaagaacca gacatagaag tatgtgctta tgatccacat gttgaattag attttgtgga    16140
acatgatatg tcacatgctg tcaaagacgc atcgctagta ttgattttaa gtgaccactc    16200
agaatttaaa aatttatcgg acagtcattt tgataaaatg aagcataaag tgattttga    16260 tacaaaaaat gttgtgaaat catcatttga agatgtatcg tattataatt atggcaatat    16320
atttaatttt atcgacaaat aa                                            16342
```

<210> SEQ ID NO 8
<211> LENGTH: 29
<212> TYPE: DNA
<213> ORGANISM: PCR primer

<400> SEQUENCE: 8
ggatcccttt tacctgcacc aggcttttc                                     29

```
<210> SEQ ID NO 9
<211> LENGTH: 27
<212> TYPE: DNA
<213> ORGANISM: PCR primer

<400> SEQUENCE: 9
ccatggctct aaagtagtaa tagtttg                                           27

<210> SEQ ID NO 10
<211> LENGTH: 36
<212> TYPE: DNA
<213> ORGANISM: PCR primer

<400> SEQUENCE: 10
ttctaatgta ctttccatat aaacctccta ttttcc                                 36

<210> SEQ ID NO 11
<211> LENGTH: 36
<212> TYPE: DNA
<213> ORGANISM: PCR primer

<400> SEQUENCE: 11
aaataggagg tttatatgga aagtacatta gaatta                                 36

<210> SEQ ID NO 12
<211> LENGTH: 25
<212> TYPE: DNA
<213> ORGANISM: PCR primer

<400> SEQUENCE: 12
gaattcgagt ctacaagcga ttaaa                                             25

<210> SEQ ID NO 13
<211> LENGTH: 30
<212> TYPE: DNA
<213> ORGANISM: PCR primer

<400> SEQUENCE: 13
cggccatggc cacagtataa attatatcag                                        30
```